US006733883B2

(12) United States Patent
Percec

(10) Patent No.: US 6,733,883 B2
(45) Date of Patent: May 11, 2004

(54) FLUORINATED DENDRONS AND SELF-ORGANIZING ULTRAHIGH DENSITY NANOCYLINDER COMPOSITIONS

(75) Inventor: Virgil Percec, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/291,362

(22) Filed: Nov. 12, 2002

(65) Prior Publication Data

US 2004/0062927 A1 Apr. 1, 2004

Related U.S. Application Data

(60) Provisional application No. 60/411,367, filed on Sep. 18, 2002.

(51) Int. Cl.[7] .................................................. B32B 5/16
(52) U.S. Cl. ........................ 428/403; 428/404; 427/212; 427/213.31; 427/215; 427/372.2; 427/374.1; 427/384; 570/123; 570/127; 570/128; 570/130; 570/182; 570/187
(58) Field of Search ................................. 428/403, 404; 570/123, 127, 129, 130, 182, 187; 427/212, 213.31, 215, 372.2, 374.1, 389

(56) References Cited

U.S. PATENT DOCUMENTS

| | | | |
|---|---|---|---|
| 5,886,110 A | 3/1999 | Gozzini et al. | |
| 6,020,457 A | 2/2000 | Klimash et al. | |
| 6,077,500 A | 6/2000 | Dvornic et al. | |
| 6,312,809 B1 | 11/2001 | Crooks et al. | |
| 6,448,301 B1 * | 9/2002 | Gaddam et al. | 522/6 |

* cited by examiner

Primary Examiner—Leszek Kiliman
(74) Attorney, Agent, or Firm—Nath & Associates PLLC; Gary M. Nath; Lee C. Heiman

(57) ABSTRACT

This invention relates to novel fluorinated dendrons and to a universal strategy for producing functional fluorinated dendrons programmed to self-assemble into supramolecular nanocylinder compositions containing p-stacks of high electron or hole mobility donors (D), acceptors (A), or D-A complexes in the core. Such nanocylinder compositions are uniquely applicable to devices spanning from single supramolecule to nanoscopic and to macroscopic scales including transistors, photovoltaics, photoconductors, photorefractives, light emissives, and optoelectronics.

10 Claims, 6 Drawing Sheets

Figure 2(a)
Figure 2(b)
Figure 2(c)
Figure 2(d)
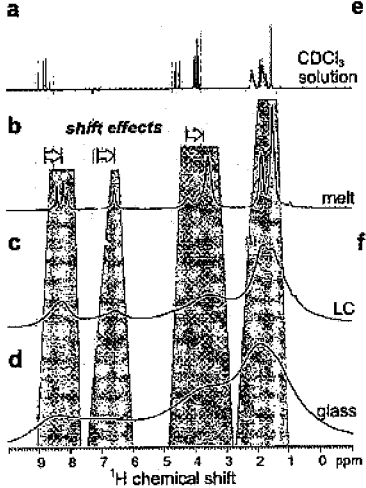
Figure 2(e)
Figure 2(f)
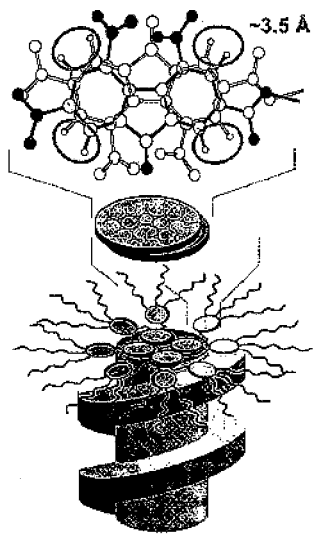

Figure 3(a)
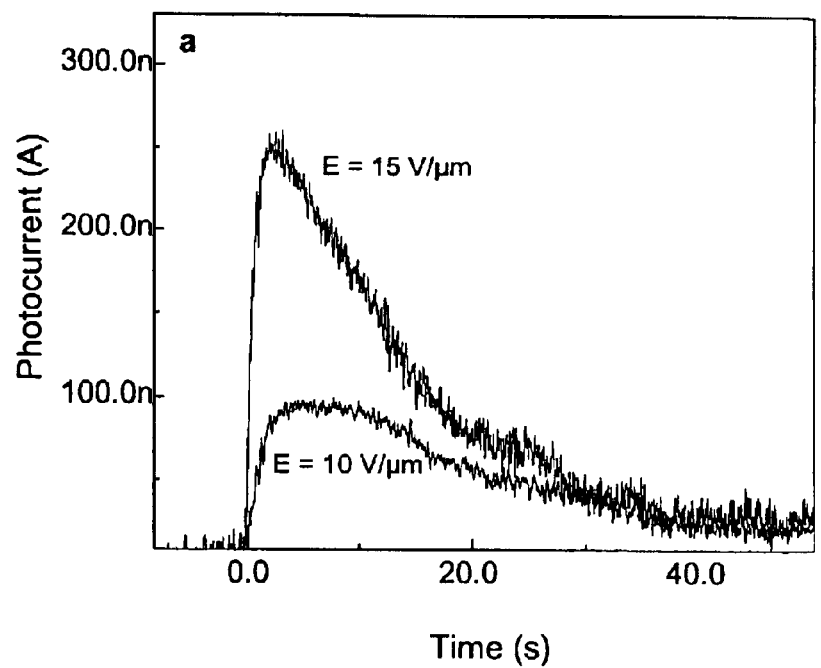
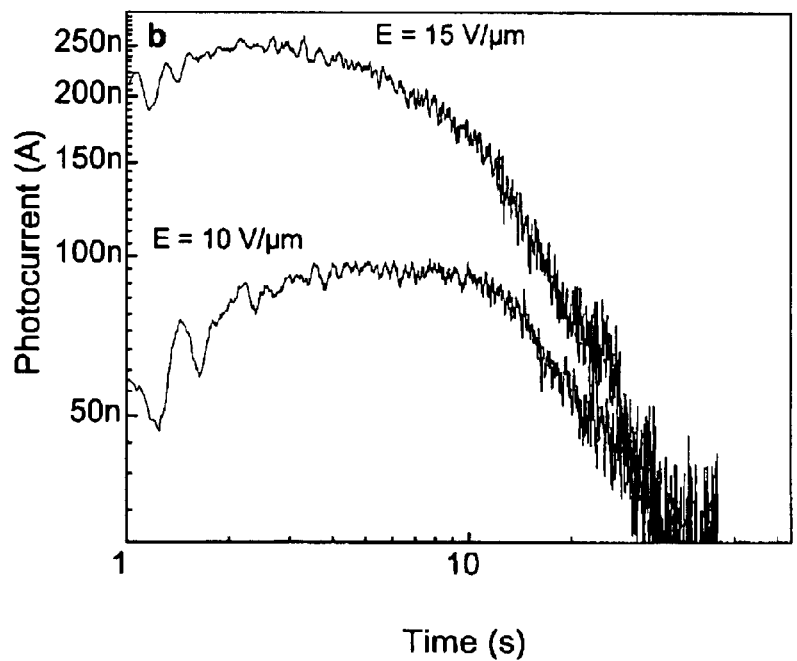
Figure 3(b)

Figure 4(a)
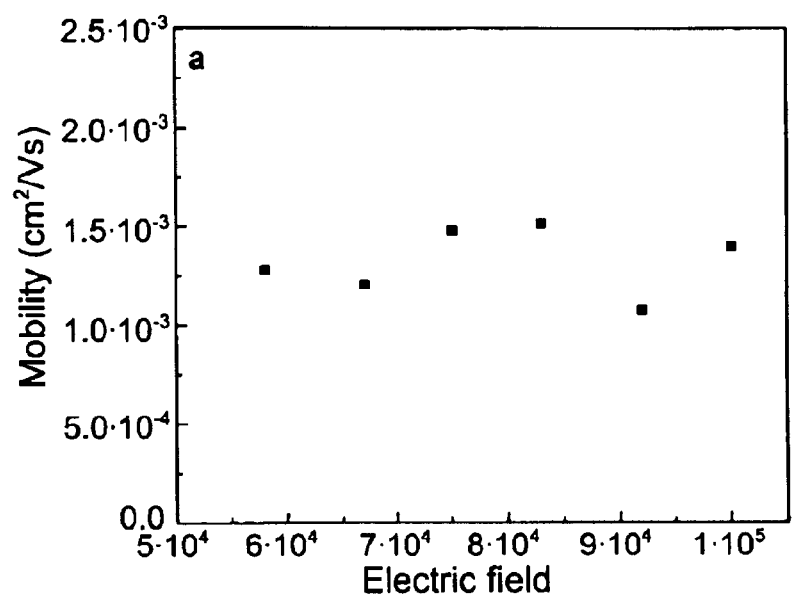
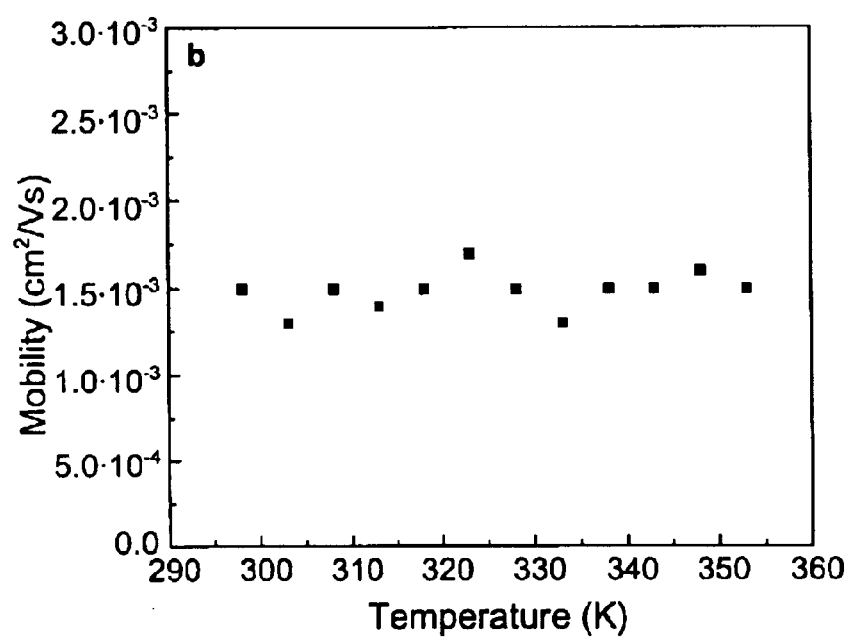
Figure 4(b)

FLUORINATED DENDRONS AND SELF-ORGANIZING ULTRAHIGH DENSITY NANOCYLINDER COMPOSITIONS

This application claims the benefit of U.S. Provisional Patent Application No. 60/411,367, filed Sep. 18, 2002, the contents of which is hereby incorporated by reference in its entirety.

BACKGROUND OF THE INVENTION

1. Field of the Invention

The present invention relates to novel fluorinated dendrons and to a method for producing functional fluorinated dendrons programmed to self-assemble into supramolecular nanocylinder compositions containing p-stacks of high electron or hole mobility donors (D), acceptors (A), or D-A complexes in the core. Such nanocylinder compositions are uniquely useful in devices such as transistors, photovoltaics, photoconductors, photorefractives, light emissives, and optoelectronics.

2. Background

Self-organized organic nanostructures with controlled optoelectronic properties that facilitate ultrahigh density nanopatterning have been attempted to be developed for molecular electronics. In this regard, charge carrier mobility ($\mu$) in organic materials appears to be mediated by p-stacking of conjugated groups, a principle resembling that of base pairs in DNA. Examples are disc- and rod-like molecules stacked in discotic hexagonal and calamitic liquid crystals (LCs), and acenes in single crystals. The development of these structures has required the synthesis of novel complex molecules and the elaboration of new processing techniques for LCs and single crystals.

The discovery of the first organic conducting polymer, polyacetylene, initiated early work relating to molecular optoelectronics. However, further work has required the development of new organic systems that exhibit higher processability, efficiency, $\mu$, density of active elements per square centimeter, mechanical integrity, and lower costs than inorganic analogues. For example, amorphous organic polymers like poly(-vinyl-carbazole) have good mechanical properties, but their $\mu$ is very low ($10^{-8}$–$10^{-6}$ cm$^2 \cdot$V$^{-1} \cdot$s$^{-1}$). Single crystals have high $\mu$ ($10^{-1}$ cm$^2 \cdot$V$^{-1} \cdot$s$^{-1}$) but are difficult to fabricate. In 1994, discotic hexagonal LCs based on aromatic molecules such as triphenylene were shown to exhibit u approaching those of single crystals. However, their effectiveness has been hindered by the multistep synthesis of each disc, their different phase behavior, and their complex processability.

The general state of the art relating to dendritic polymers and their uses, and compounds having electron-accepting or electron-donating systems, is described in the following U.S. Patents.

U.S. Pat. No. 5,731,095 to Milco, et al., issued Mar. 24, 1998, discloses water-soluble or water-dispersible fluorine-containing dendritic polymer surfactants.

U.S. Pat. No. 5,872,255 to Attias, et al. issued Feb. 16, 1999, discloses conjugated compounds having electron-withdrawing or electron-donating systems, and the use of said compounds or of any material which includes them in electronic, optoelectronic, nonlinear optical, and electrooptical devices.

U.S. Pat. No. 5,886,110 to Gozzini, et al. issued Mar. 23, 1999, discloses branched, dendrimeric macromolecules having a central nucleus and a series of polyoxaalkylene chains that radiate from the nucleus and spread into the surrounding space, branching in a cascade fashion until the desired size results.

U.S. Pat. No. 6,020,457 to Klimash, et al. issued Feb. 1, 2000, discloses dendritic polymers containing disulfide functional groups which are essentially inert under non-reducing conditions, but which form sulfhydryl groups upon being subjected to a reducing agent, and their uses in the formation of differentiated dendrimers, formation of binding reagents for diagnostics, drug delivery, gene therapy and magnetic resins imaging, and in the preparation of self-assembled dendrimer monolayers on quartz crystal resonators to provide dendrimer-modified electrodes which are useful for detecting various ions or molecules.

U.S. Pat. No. 6,051,669 to Attias, et al., issued Apr. 18, 2000, discloses conjugated polymer compounds having electron-withdrawing or electron-donating systems, and the use of said compounds or of any material which includes them in electronic, optoelectronic, nonlinear optical, and electrooptical devices.

U.S. Pat. No. 6,077,500 to Dvornic, et al., issued Jun. 20, 2000, discloses higher generation radially layered copolymeric dendrimers having a hydrophilic poly(amidoamine) or a hydrophilic poly(propyleneimine) interior and a hydrophobic organosilicon exterior, and their uses for delivering active species for use in catalysis, pharmaceutical applications, drug delivery, gene therapy, personal care, and agricultural products.

U.S. Pat. No. 6,136,921 to Hsieh, et al., issued Oct. 24, 2000, discloses a coupled polymer which is prepared by reacting a living alkali metal-terminated polymer with a coupling agent, having good rubbery physical properties, transparency, and wear resistance.

U.S. Pat. No. 6,312,809 to Crooks, et al., issued Nov. 6, 2001, discloses a substrate having a dendrimer monolayer film covalently bonded to the surface, and uses as a chemically sensitive surface, such as in chemical sensors.

The prior art has been ineffective in formulating effective structures that have higher processability, efficiency, $\mu$, density of active elements per square centimeter, mechanical integrity, and lower costs than inorganic analogues. Surprisingly, the present inventive subject matter overcomes these deficiencies in the prior art and is directed to the production of novel functional fluorinated dendrons which are programmed to self-assemble into supramolecular nanocylinder compositions containing p-stacks of high electron ($\mu_e$) or hole ($\mu_h$) mobility donors (D), acceptors (A), or D-A complexes in the core. The co-assembly of D- or A-dendrons with amorphous polymers containing A or D side groups, respectively, incorporates the polymer backbone in the center of the cylinder via p-stacks of D-A interactions and enhances u of the resulting polymer. These supramolecular cylinders self-process into homeotropically aligned hexagonal and rectangular columnar LCs that pattern ultrahigh density arrays (up to 4.5×10$^{12}$ cylinders per square centimeter) between electrodes. Below glass transition temperature, a complex and organized optoelectronic matter of cylinders composed of helical dendrons jacketing stacks of aromatic groups with even higher, essentially insensitive to ionic impurities, is produced. Such arrays are uniquely applicable to devices having a broad range of sizes. In particular, such compositions are used in devices spanning the range from single supramolecule, to nanoscopic, to macroscopic. Useful devices for including said compositions are transistors, photovoltaics, photoconductors, photorefractives, light emissives, and optoelectronics, which has not heretofore been possible.

SUMMARY OF THE INVENTION

The present invention relates to a compound of formula I

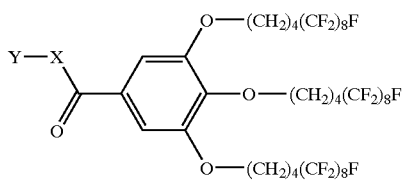

wherein:

X is Z—$(CH_2CH_2O)_n$—, where n is 1–6, or Z—$(CH_2)_mO$—, where m is 1–9;

Y is selected from the group consisting of pentalene, indene, naphthalene, azulene, heptalene, biphenylene, indacene, acenaphthylene, fluorene, phenalene, phenanthrene, anthrcene, fluoranthene, acephenanthrylene, aceanthrylene, triphenylene, pyrene, chrysene, and naphthacene, wherein said Y is optionally substituted with 1–6 substituents selected from the group consisting of nitro, nitroso, carbonyl, carboxy, oxo, hydroxy, fluoro, perfluoro, chloro, perchloro, bromo, perbromo, phospho, phosphono, phosphinyl, sulfo, sulfonyl, sulfinyl, trifluoromethyl, trifluoromethylsulfonyl, and trimethylsulfonyl, and wherein 1–4 carbon atom(s) of said Y is/are optionally replaced by N, NH, O, or S; and Z is selected from the group consisting of a direct bond, —C(O)O—, ($C_1$-$C_6$ alkyl)—C(O)O—, ($C_2$-$C_6$ alkenyl)—C(O)O—, and ($C_2$-$C_6$ alkynyl)—C(O)O—.

The present invention further relates to a process for making a stacked nanocylinder composition having a mobility donor complex, a mobility acceptor complex, or a mobility donor-acceptor complex in its core, which comprises:

(a) heating semi-fluorinated dendrons incorporating selected dendron apex moiety(ies) and side group(s) having donor, acceptor, or donor-acceptor characteristics to an isotropic phase temperature;

(b) filling a substrate with said isotropic phase dendrons; and (c) cooling said dendrons to a liquid crystalline phase temperature.

The present invention further relates to the stacked nanocylinder composition described above, made by the process which comprises the steps of:

(a) heating semi-fluorinated dendrons incorporating selected dendron apex moiety(ies) and side group(s) having donor, acceptor, or donor-acceptor characteristics to an isotropic phase temperature;

(b) filling an indium tin oxide coated glass substrate with said isotropic phase dendrons; and (c) cooling said dendrons to a liquid crystalline phase temperature at a rate of about 0.1° C. per minute, in the presence of a magnetic field of about 1 tesla.

BRIEF DESCRIPTION OF THE DRAWINGS

FIG. 2(a) is a graph which depicts the $^1$H NMR spectra of compound A1 at 22° C.

FIG. 2(b) is a graph which depicts the $^1$H NMR spectra of compound A1 in the isotropic melt state at 120° C.

FIG. 2(c) is a graph which depicts the $^1$H NMR spectra of compound A1 in the LC state at 75° C.

FIG. 2(d) is a graph which depicts the $^1$H NMR spectra of compound A1 in the glassy state at 25° C.

FIG. 2(e) is a drawing which depicts sandwich-type stacking of nitro-fluorenone moieties.

FIG. 2(f) is a drawing which depicts the structure of supramolecular cylinders of the present invention, with stacks of fluorenone sandwiches in the center, jacketed by helical dendrons.

FIGS. 3(a) and 3(b) are graphs which depict hole photocurrent transients plotted on (a) linear and (b) double logarithmic scales for compound D4 at 70° C.

FIGS. 4(a) and 4(b) are graphs which depict (a) electric field and (b) temperature dependence of the carrier mobility of compound D4 in the $\Phi_h$ phase.

DETAILED DESCRIPTION OF THE INVENTION

Definitions

Figures 1, 1A, 1B, 1C:
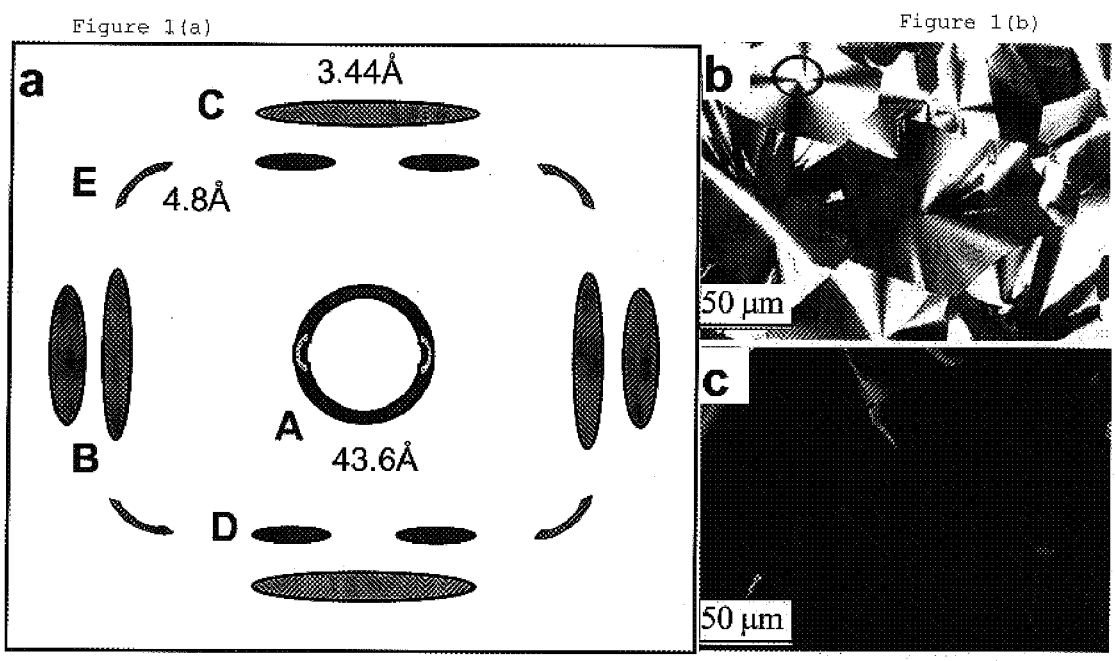
FIG. 1(a) is a drawing which depicts the spacial correlation between elements of compound A1 in a supramolecular cylinder.
FIG. 1(b) is a photograph which depicts thermal optical polarized microscopy (TOPM) of the texture of compound D4 in the liquid crystalline state after cooling at 20° C./minute from the isotropic phase, showing defect characteristics.
FIG. 1(c) is a photograph which depicts TOPM of a homeotropically aligned compound D4 after cooling at 0.1° C./minute.
Figure 5:
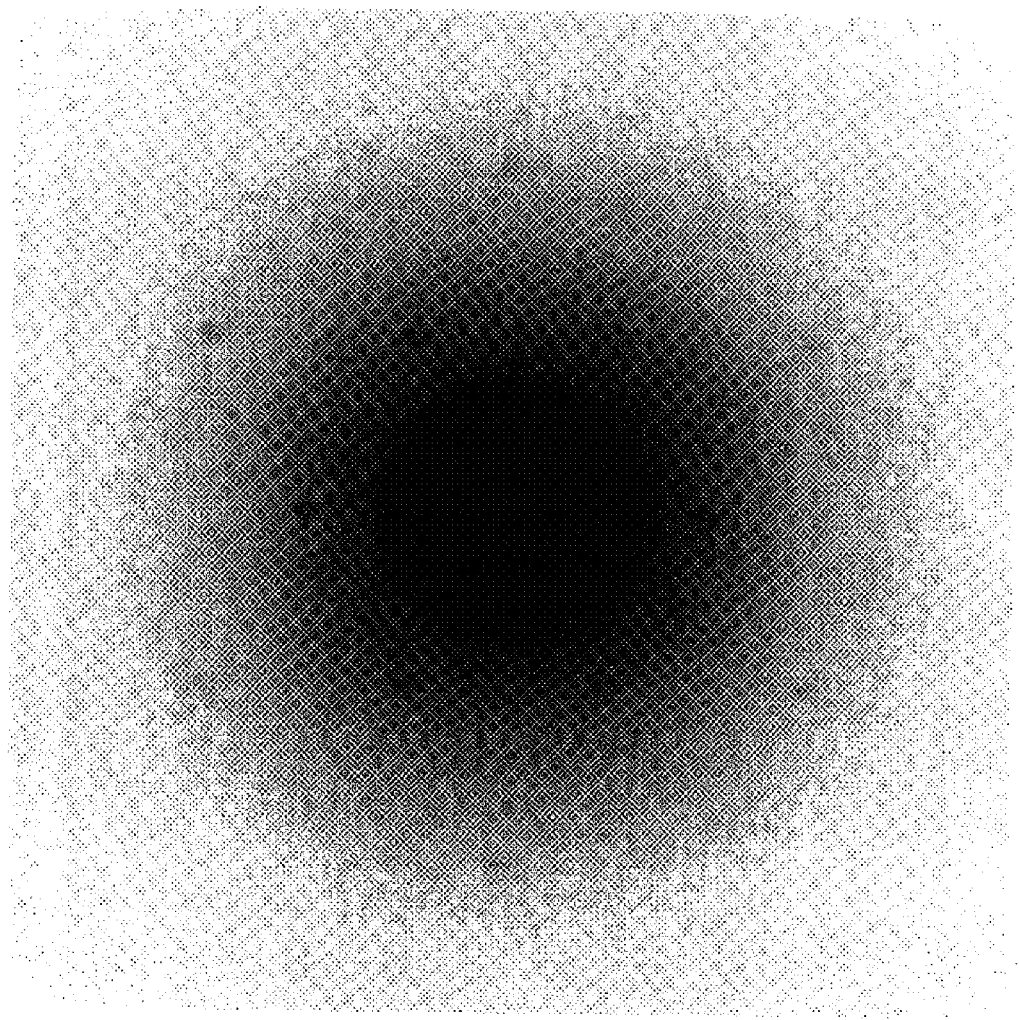
FIG. 5 is a photograph which depicts the electron diffraction (ED) of compound D4.
Figure 6:
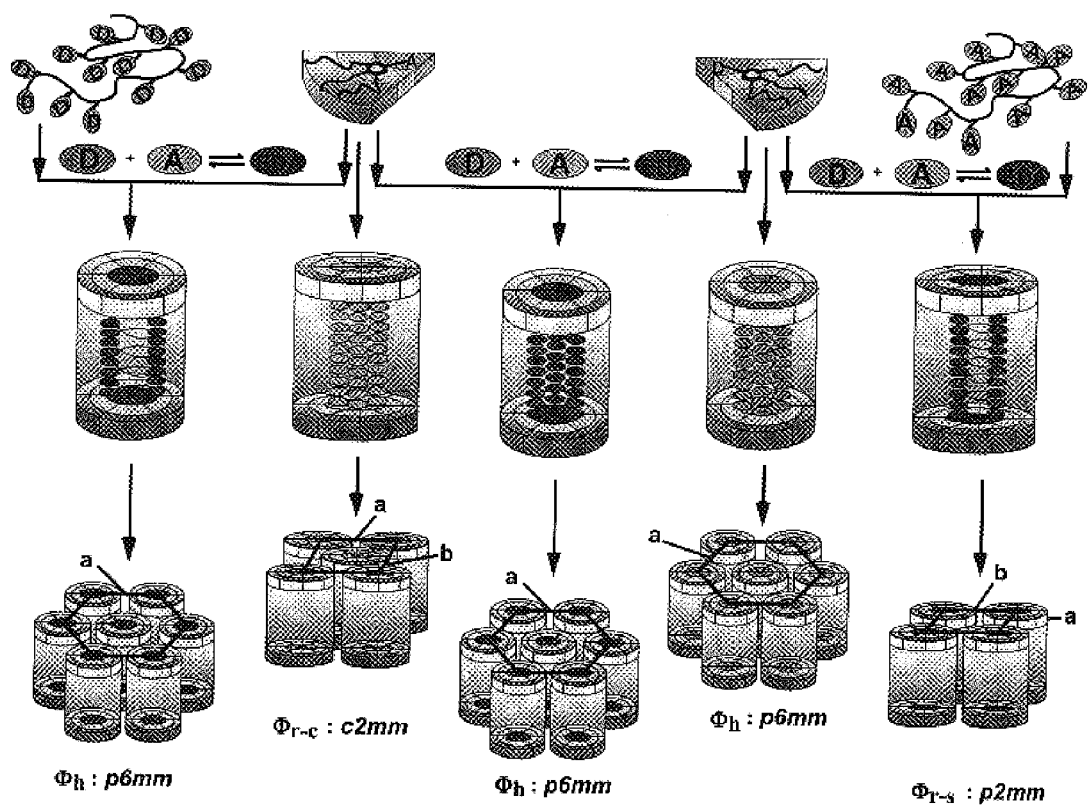
FIG. 6 is a drawing which depicts self-assembly, co-assembly, and self-organization of dendrons containing donor (D) and acceptor (A) groups with amorphous polymers containing D and A groups.

The term "replaced" as used herein refers to the situation wherein an atom takes the place of another atom in the chemical formula of a compound. For example, replacement of the carbon atom at the 9-position of fluorene with a nitrogen atom produces carbazole.

The term "substituent" as used herein refers to an atom or group which is added to a chemical entity by replacing one or more hydrogen atom(s); monovalent groups replace one hydrogen atom, bivalent groups replace two hydrogen atoms, and so forth.

The term "$\mu$" as used herein refers to charge carrier mobility, or velocity, in an electric field.

The term "$\mu_e$" as used herein refers to electron mobility in an electric field.

The term "$\mu_h$" as used herein refers to hole mobility in an electric field.

The term "p-stack" or "π-stack" as used herein refers to the hydrophobic interaction which occurs between aromatic or aromatic heterocyclic side chains and produces a cloud of free electrons from the pi-orbitals of atoms composing the stacked structure.

The term "donor" or "D" as used herein refers to a substance which produces an increase in the electron density in a material, and a corresponding decrease in the hole concentration. Similarly, the term "acceptor" or "A" as used herein refers to a substance which produces an decrease in the electron density in a material, and a corresponding increase in the hole concentration. "D-A complexes" refers to a material in which both donor and acceptor substances are present.

The term "isotropic phase" as used herein refers to the phase of matter in which the molecules are randomly aligned, exhibit no long range order, and have a low viscosity. The characteristic lack of orientational order of the isotropic phase is that of a traditional liquid phase.

The term "liquid crystalline phase" as used herein refers to a phase of matter in which the molecules tend to point along a common axis, exhibit long range orientational order, and wherein the average orientation may be manipulated with an electric field. The characteristic orientational order of the liquid crystal state is between the traditional solid and liquid phases.

COMPOUNDS OF THE PRESENT INVENTION

The present invention relates to a compound of formula I

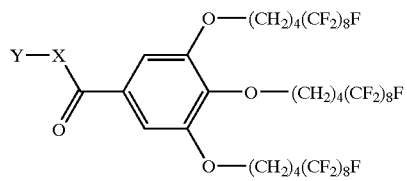

I wherein:
- X is Z—$(CH_2CH_2O)_n$, where n is 1–6, or Z—$(CH_2)_mO$, where m is 1–9;
- Y is selected from the group consisting of pentalene, indene, naphthalene, azulene, heptalene, biphenylene, indacene, acenaphthylene, fluorene, phenalene, phenanthrene, anthrcene, fluoranthene, acephenanthrylene, aceanthrylene, triphenylene, pyrene, chrysene, and naphthacene,
  - wherein said Y is optionally substituted with 1–6 substituents selected from the group consisting of nitro, nitroso, carbonyl, carboxy, oxo, hydroxy, fluoro, perfluoro, chloro, perchloro, bromo, perbromo, phospho, phosphono, phosphinyl, sulfo, sulfonyl, sulfinyl, trifluoromethyl, trifluoromethylsulfonyl, and trimethylsulfonyl,
  - and wherein 1–4 carbon atom(s) of said Y is/are optionally replaced by N, NH, O, or S; and
- Z is selected from the group consisting of a direct bond, —C(O)O—, ($C_1$-$C_6$ alkyl)—C(O)O—, ($C_2$-$C_6$ alkenyl)—C(O)O—, and ($C_2$-$C_6$ alkynyl)—C(O)O—.

In a preferred embodiment of the compound of Formula I:

- X is Z—$(CH_2CH_2O)_n$, where n is 1–3, or Z—$(CH_2)_mO$, where m is 2–4;
- Y is selected from the group consisting of naphthalene, indacene, fluorene, phenanthrene, anthrcene, and pyrene,
  - wherein said Y is optionally substituted with 1–4 substituents selected from the group consisting of nitro, carboxy, oxo, phospho, and sulfo,
  - and wherein one carbon atom of said Y is optionally replaced by N or NH; and
- Z is selected from the group consisting of a direct bond, —C(O)O—, or ($C_1$-$C_6$ alkyl)—C(O)O—.

In a more preferred embodiment of the compound of Formula I:

- X is selected from the group consisting of diethylene glycol and tetraethylene glycol;
- Y is selected from the group consisting of carbazole, naphthalene, pyrene, and 4,5,7-trinitrofluorenone-2-carboxylic acid; and
- Z is selected from the group consisting of a direct bond, —C(O)O—, and —$CH_2$—C(O)O—.

In the most preferred embodiment of the compounds of Formula I, said compound is selected from the group consisting of:

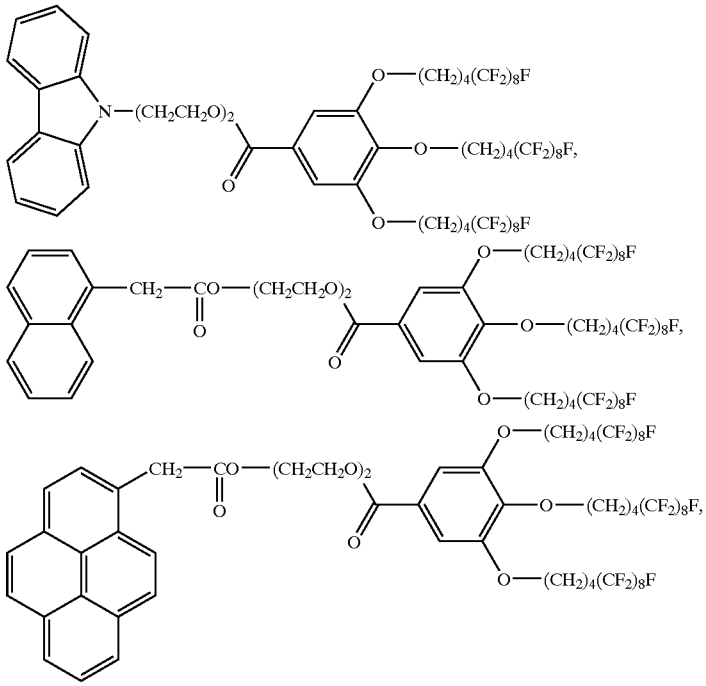

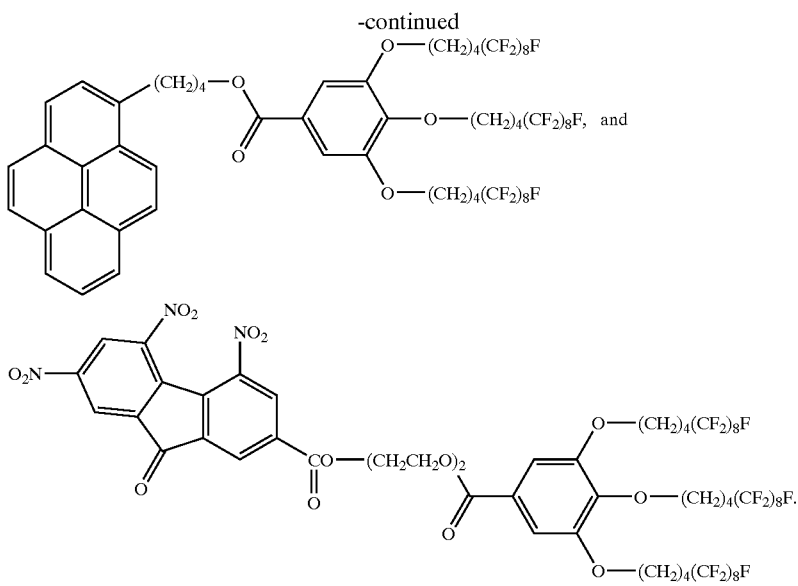

and

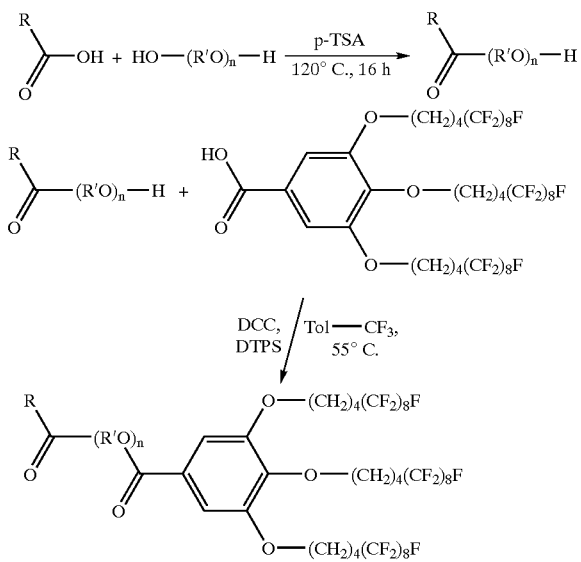

SYNTHESIS OF COMPOUNDS OF THE INVENTION

A representative mobility donor fluorinated dendron of the present invention may be readily prepared by standard techniques of chemistry, utilizing the general synthetic pathway depicted below in Scheme I.

Utilizing the general pathway to a representative mobility donor fluorinated dendron of the present invention as shown in Scheme I, compounds may be prepared using 3,4,5-tris-(12,12,12,11,11,10,10,9,9,8,8,7,7,6,6,5,5-heptadecafluoro-n-dodecan-1-yloxy)-benzoic acid as a starting material. These intermediates are then reacted with, for example, an alcohol of the desired apex moiety, such as 2-(2-carbazol-9yl-ethoxy)-ethanol, to obtain the compounds of the invention.

In the preparation of the compounds of the invention, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the present invention.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

PROCESSES AND PRODUCTS OF THE PRESENT INVENTION

The present invention further relates to a process for making a stacked nanocylinder composition having a mobility donor complex, a mobility acceptor complex, or a mobility donor-acceptor complex in its core, which comprises:

(a) heating semi-fluorinated dendrons incorporating selected dendron apex moiety(ies) and side group(s) having donor, acceptor, or donor-acceptor characteristics to an isotropic phase temperature;

(b) filling a substrate with said isotropic phase dendrons; and (c) cooling said dendrons to a liquid crystalline phase temperature.

In a preferred embodiment, said cooling step is in the presence of a magnetic field of about 1 tesla.

In another preferred embodiment, said cooling is at a rate of about 0.1° C. per minute.

In another preferred embodiment, said substrate is an indium tin oxide coated glass substrate.

In another preferred embodiment, the substrate cell size of said nanocylinder composition is controlled by mylar spacers.

The present invention further relates to the stacked nanocylinder composition described above, made by the process which comprises the steps of:

(a) heating semi-fluorinated dendrons incorporating selected dendron apex moiety(ies) and side group(s) having donor, acceptor, or donor-acceptor characteristics to an isotropic phase temperature;

(b) filling an indium tin oxide coated glass substrate with said isotropic phase dendrons; and (c) cooling said dendrons to a liquid crystalline phase temperature at a rate of about 0.1° C. per minute, in the presence of a magnetic field of about 1 tesla.

In order to address the need for self-organized organic nanostructures with controlled optoelectronic properties which facilitate ultrahigh density nanopatterning, we have elaborated a library based on a semifluorinated dendron that is functionalized at its apex with a diversity of D and A groups. The resulting functional dendrons are programmed to self-assemble into cylinders containing the optoelectronic element in their core. The supramolecular cylinders self-organize into homeotropically aligned hexagonal ($\Phi_h$) or rectangular ($\Phi_{r-c}$ and $\Phi_{r-s}$) LCs.

The combination of self-assembly, insensitivity to ionic impurities, ease of processability, and high charge carrier mobility is unexpected, resulting in an unprecedented, simple, and practical strategy to increase the $\mu$ values of conventional D, A, and EDA low molar mass and macromolecular systems to levels previously obtained only by complex discotic molecules. The new supramolecular cylindrical architecture, and the universal self-processability of these programmed dendrons into large homeotropic domains (100 μm to cm size) (FIGS. 1b, c), create new frameworks for dendritic molecules and open new perspectives in the world of nanoscience and nanotechnology. In addition to the utility described above in relation to optoelectronic devices employing LCs, such nanocylinder compositions are expected to be uniquely useful in devices such as transistors, photovoltaics, photoconductors, photorefractives, and light emissives because of their uniquely high charge carrier mobility and relative ease of synthesis and handling.

EXAMPLES

The following examples are illustrative of the present invention and are not intended to be limitations thereon. Unless otherwise indicated, all percentages are based upon 100% by weight of the final composition. All starting materials, reagents, and solvents were commercially available and were used either as obtained from chemical suppliers, synthesized according to known literature procedures, and/or washed, dried, distilled, recrystallized, and/or purified before use.

Example 1

Preparation of {2-[2-(Carbazol-9-yl)-ethoxy]-ethyl}3,4,5-tris-(12,12,12,11,11,10,10,9,9,8,8,7,7,6,6,5,5-heptadecafluoro-n-dodecan-1-yloxy)-benzoate (D1)

The synthesis of a mobility donor fluorinated dendron D1 of the present invention is as shown in the Scheme below.

D1 is prepared using 3,4,5-tris-(12,12,12,11,11,10,10,9,9,8,8,7,7,6,6,5,5-heptadecafluoro-n-dodecan-1-yloxy)-benzoic acid as a starting material. The intermediate is then reacted with an alcohol of the desired apex moiety, 2-(2-carbazol-9yl-ethoxy)-ethanol, to obtain the compound of the invention.

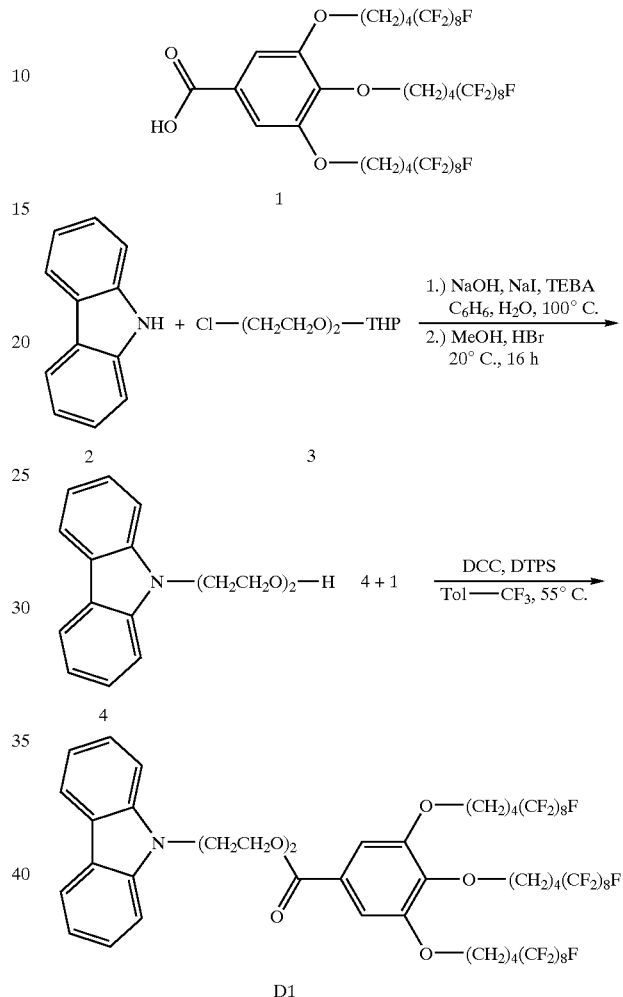

More particularly, compound D1 is synthesized as follows:

2-(2-Carbazol-9-yl-ethoxy)-ethanol (4): To a flask containing 100 ml benzene, 100 ml 50% NaOH, was added carbazole (2) (20 g, 0.12 mmol), 4 g benzyltriethylammonium chloride (TEBA), 1 g of NaI and 2-[2-(2-chloroethoxy)-ethoxy]-tetrahydropyran (3) (38 g, 0.12 mmol) under $N_2$. The mixture was refluxed for 6 h.

The reaction mixture was diluted with 100 ml of benzene and the organic phase was separated, washed with $H_2O$, dried over anhydrous $MgSO_4$, and filtered through acidic $Al_2O_3$. After the removal of benzene, the crude product was suspended in 400 ml MeOH followed by addition of 2 ml of concentrated HBr. After the reaction mixture was stirred at 20° C. for 16 h, it was neutralized by 10% aqueous NaOH and MeOH was distilled. The crude product was washed with $H_2O$ several times, dried under vacuum and was further purified by recrystallization from MeOH twice to yield 23 g (75%) of 4 as white crystals. Purity: 99% (HPLC). TLC: Rf=0.18 (hexanes/EtOAc: 3/1). mp 80–81° C. $^1$H NMR (200 MHz, $CD_3COCD_3$, 20° C.): d 8.1 (d, 2H, J=7.8 Hz), 7.4 (m, 4H), 7.25 (m, 2H), 4.4 (t, 2H, J=5.7 Hz), 3.8 (t, 2H, J=5.7 Hz), 3.5 (t, 2H, J=5.0 Hz), 3.4 (t, 2H, J=5.0 Hz). $^{13}$C NMR (50 MHz, CD$_3$COCD$_3$, 20° C.): d 140.9, 125.8, 123.0, 120.3, 119.1, 109.5, 72.8, 69.4, 61.1, 43.1.

{2-[2-(Carbazol-9-yl)-ethoxy]-ethyl}3,4,5-tris-(12,12,12,11,11,10,10,9,9,8,8,7,7,6,6,5,5-heptadecafluoro-n-dodecan-1-yloxy)-benzoate (D1): A mixture containing 1 (1.0 g, 0.63 mmol) and 4 (0.17 g, 0.66 mmol) was dissolved in α,α,α-trifluorotoluene (10 ml) and stirred over 1 g of molecular sieves (4 Å) for 1 h under N$_2$. DCC (0.260 g, 1.26 mmol) and DPTS (40 mg, 0.13 mmol) were added to the reaction mixture. The reaction mixture was stirred at 45° C. for 24 h under N$_2$. The progress of the reaction was monitored by TLC. The reaction mixture was filtered through a sintered filter to remove the molecular sieves which were subsequently washed several times with CH$_2$Cl$_2$. The organic solution was concentrated and precipitated in MeOH four times from CH$_2$Cl$_2$ solution. Purification of the crude product was performed by column chromatography (SiO$_2$/CH$_2$Cl$_2$), followed by precipitation in MeOH from CH$_2$Cl$_2$ solution to yield 0.92 g (82%) of D1 as white crystals. $^1$H NMR (CDCl$_3$, 500 MHz, 20° C.): d 8.1 (d, 2H J=7.7 Hz), 7.4 (m, 4H), 7.2 (m, 6H), 4.5 (t, 4H, J=5.9 Hz), 4.4 (t, 2H, J=4.7 Hz), 4.2–4.0 (overlapped t, 8H), 3.7 (t, 2H J=4.7 Hz), 2.3–2.1 (m, 6H), 1.8 (m, 12H); $^{13}$C NMR (CDCl$_3$, 125 MHz, 20° C.): d 166.7, 152.6, 142.1, 140.8, 125.7, 125.2, 121.9, 120.5–108.2 (several CF multipletts), 119.6, 119.2, 108.8, 108.3, 72.7, 69.6, 69.4, 68.5, 64.1, 43.3, 30.6 (t, J$_{CF}$=22 Hz), 29.8, 28.8, 17.4, 17.2. Anal. Calcd. for C$_{57}$H$_{42}$NF$_{51}$O$_6$: C, 38.73; H, 2.31; F, 52.95; N, 0.77. Found: C, 38.68; H, 2.12; N, 0.79. DSC: 1st Heating k 39 (2.3) k 53 (9.6) Φ$_h$ 75 (1.0) i, 1st cooling i 71 (0.8) Φ$_h$ 13 (4.9) k 6 g, 2nd heating g 13 k 21 (5.0) Φ$_h$ 75 (0.8) i.

Example 2

Preparation of {2-[2-((1-Naphthyl)-acetoxy)-ethoxy]-ethyl}3,4,5-tris-(12,12,12,11,11,10,10,9,9,8,8,7,7,6,6,5,5-heptadecafluoro-n-dodecan-1-yloxy)-benzoate (D2)

As depicted in the Scheme below, (2-hydroxyethoxy)-ethyl (1-naphthyl)-acetate is reacted with 3,4,5-tris-(12,12,12,11,11,10,10,9,9,8,8,7,7,6,6,5,5-heptadecafluoro-n-dodecan-1-yloxy)-benzoic acid to produce a second representative mobility donor fluorinated dendron of the present invention, compound D2.

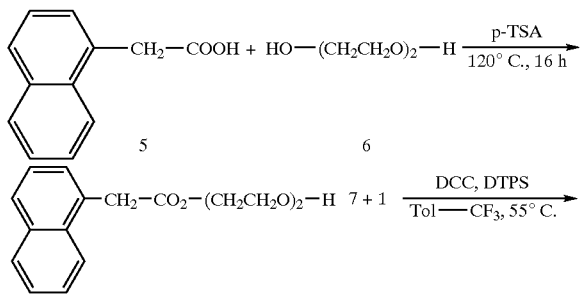

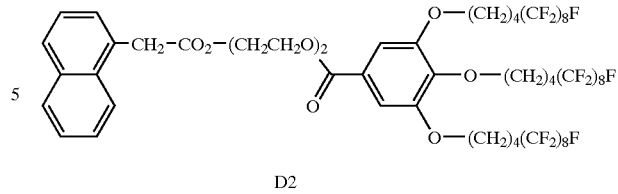

D2

More particularly, compound D2 is synthesized as follows:

(2-Hydroxyethoxy)-ethyl (1-naphthyl)-acetate (7): A mixture of 1-naphthylacetic acid (5) (2.0 g, 0.011 mol), PTSA (200 mg, 1.1 mmol), and diethylene glycol (6) (8 ml, 72.8 mmol) was stirred at 120° C. under N$_2$. The reaction mixture became homogeneous after 1 h, and the stirring was continued for 15 h. After the reaction was completed (confirmed by TLC), the reaction mixture was poured into 50 ml of icewater mixture. The aqueous reaction mixture was extracted by EtOAc (3×50 ml) and dried over anhydrous MgSO$_4$. The crude product was purified by column chromatography (SiO$_2$, EtOAc/hexanes: 8/2) to yield 2.25 g (76%) of 7 as a colorless oil. $^1$H NMR (CDCl$_3$, 500 MHz, 20° C.): d 7.83 (d, 1H, J=7.1 Hz ), 7.72–7.64 (m, 2H), 7.40–7.26 (m, 4H), 4.11 (t, 2H, J=4.7Hz), 3.96 (s, 2H), 3.46 (overlapped m, 4H), 3.26 (t, 2H, J=4.4 Hz), 1.90 (s, 1H). $^{13}$C NMR (CDCl$_3$, 90 MHz, 20° C.): d 171.7, 134.0, 132.2, 130.6, 128.9, 128.2, 126.5, 126.0, 125.7, 123.9, 72.4, 65.8, 64.2, 61.2, 39.3.

{2-[2-((1-Naphthyl)-acetoxy)-ethoxy]-ethyl}3,4,5-tris-(12,12,12,11,11,10,10,9,9,8,8,7,7,6,6,5,5-heptadecafluoro-n-dodecan-1-yloxy)-benzoate (D2): To a solution of 1 (1 g, 0.63 mmol), 7 (0.68 g, 2.5 mmol), and DPTS (50 mg, 0.17 mmol) in α,α,α-trifluorotoluene (15 ml) under N$_2$ was added DCC (300 mg, 1.5 mmol), and the reaction mixture was stirred at 45° C. for 24 h. The mixture was diluted with CH$_2$Cl$_2$ and precipitated in MeOH four times. The crude product was purified by flash column chromatography (SiO$_2$, CH$_2$Cl$_2$) and precipitated in EtOH from CH$_2$Cl$_2$ solution to yield 0.81 g (68%) of D2 as white solid. TLC: Rf=0.81 (EtOAc). Purity: 99%+(HPLC). $^1$H NMR (CDCl$_3$, 500 MHz, 20° C.): d 7.87–7.78 (overlapped d, 2H), 7.76 (d, 1H, J=6.8 Hz), 7.48–7.38 (m, 4H), 7.26 (s, 2H), 4.37 (t, 2H, J=4.4 Hz), 4.28 (t, 2H, J=4.5 Hz), 4.07 (s, 2H), 4.01 (m, 6H), 3.69 (m, 4H), 2.13 (m, 6H), 1.82 (m, 12H), $^{13}$C NMR (CDCl$_3$, 90 MHz, 20° C.): d 172.0, 166.3, 152.7, 142.1, 134.0, 130.5, 128.9, 128.3, 128.2, 126.6, 126.0, 125.6, 125.3, 123.9, 120.5–108.2 (several CF multipletts), 108.3, 72.8, 69.3, 69.1, 68.6, 64.2, 39.2, 30.8 (t, J$_{CF}$=22 Hz), 29.9, 28.9, 17.5, 17.3. FAB-MS for C$_{59}$H$_{43}$F$_{51}$O$_8$ m/z: 1871.2 [M+Na]$^+$. Anal. Calcd. for C$_{59}$H$_{43}$F$_{51}$O$_8$ C, 38.33, H, 2.34, found C, 38.42, H, 2.20. DSC: 1st heating k 24 (0.7) k 48 (8.9) Φ$_h$ 75 (0.4) i, 1st cooling i 70 (0.4) Φ$_h$ 16 (3.2) k. 2nd heating g 11 k 24 (3.0) Φ$_h$ 74 (0.4) i.

Example 3

Preparation of {2-[2-((1-Pyrenyl)-acetoxy)-ethoxy]-ethyl}3,4,5-tris-(12,12,12,11,11,10,10,9,9,8,8,7,7,6,6,5,5-heptadecafluoro-n-dodecan-1-yloxy)-benzoate (D3)

As depicted in the Scheme below, 2-(2-Hydroxyethoxy)-ethyl (1-pyrenyl)-acetate is reacted with 3,4,5-tris-(12,12,12,11,11,10,10,9,9,8,8,7,7,6,6,5,5-heptadecafluoro-n-dodecan-1-yloxy)-benzoic acid to produce compound D3.

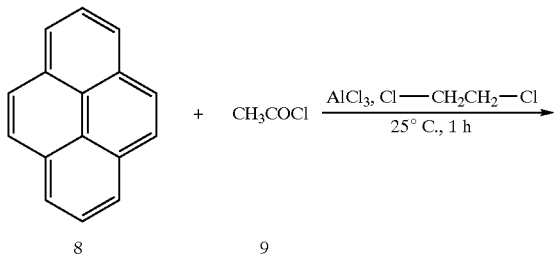
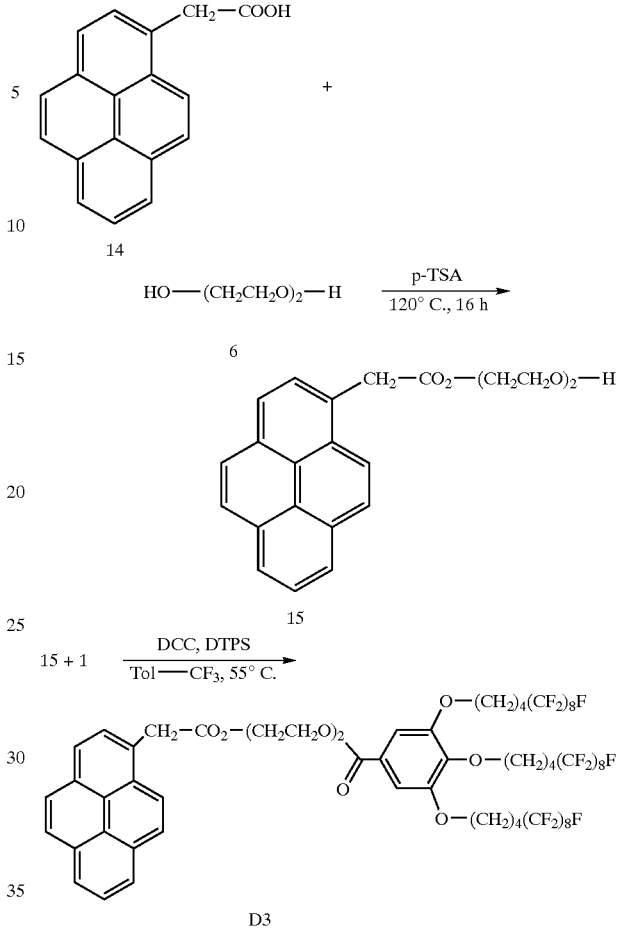
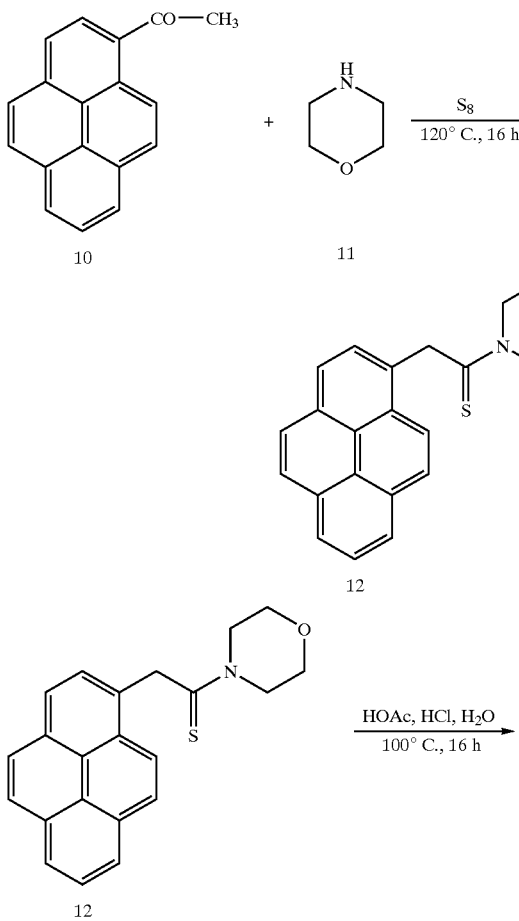
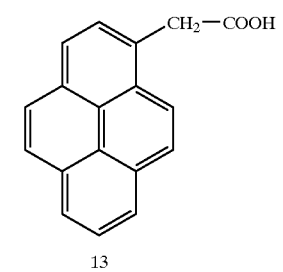

More particularly, compound D3 is synthesized as follows:

2-(2-Hydroxyethoxy)-ethyl (1-pyrenyl)-acetate (15): 1-Pyreneacetic acid (1 g, 3.85 mmol), diethylene glycol (10 ml, 91.0 mmol) and p-toluenesulfonic acid (100 mg, 0.58 mmol) were mixed and heated to 130° C. for 16 h with stirring under $N_2$. After the reaction was completed (confirmed by TLC), the reaction mixture was cooled to 20° C. and poured into 50 ml ice-water drop-wise. The aqueous reaction mixture was extracted with EtOAc (3×100 ml) and the combined organic solutions were washed with 5% aqueous KOH (2×50 ml), $H_2O$ (2×50 ml) and brine (1×50 ml), and were subsequently dried over anhydrous $MgSO_4$. The crude product was purified by column chromatography (silica gel, EtOAc/hexanes: 1/1) to yield 1.12 g (83.59%) 15 as a light green oil. Purity: 99+% (HPLC). TLC: Rf=0.17 (EtOAc/hexanes: 1/1). $^1$H NMR (250 MHz, CDCl$_3$, 20° C.): δ 8.26–7.94 (m, 9H), 4.38 (s, 2H), 4.27 (m, 2H), 3.63 (m, 2H), 3.53 (m, 2H), 3.39 (m, 2H), 2.82 (s broad, 1H). $^{13}$C NMR (125 MHz, CDCl$_3$, 20° C.): δ 171.5, 131.3, 130.8, 130.7, 129.4, 128.3, 127.9, 127.4, 127.3, 126.0, 125.3, 125.1, 125.0, 124.8, 124.7, 123.2, 72.2, 68.9, 64.1, 61.6, 39.4.

{2-[2-((1-Pyrenyl)-acetoxy)-ethoxy]-ethyl}3,4,5-tris-(12,12,12,11,11,10,10,9,9,8,8,7,7,6,6,5,5-heptadecafluoro-n-dodecan-1-yloxy)-benzoate (D3): 15 (0.40 g, 1.15 mmol), 1 (1.46 g, 0.92 mmol), DCC (0.57 g, 2.75 mmol) and DPTS (14 mg, 45.7 μmol) were dissolved in α,α,α-trifluorotoluene (20 ml) and stirred for 16 h at 55° C. under $N_2$. The solvent was evaporated and the residue was dissolved in $CH_2Cl_2$ (10 ml) and precipitated in MeOH (50 ml) 4 times. The crude product was further purified by column chromatography (silica gel, EtOAc/hexanes: 3/7) to yield 1.33 g (60.0%) of D3 as a white powder. Purity: 99+% (HPLC). TLC: Rf=0.37 (EtOAc/hexanes: 3/7). $^1$H NMR (250 MHz, $CDCl_3$, 20° C.): δ 8.21–7.89 (m, 9H), 7.22 (s, 2H), 4.35–4.28 (m overlapping, 6H), 3.95–3.93 (m, 6H), 3.72–3.67 (m, 4H), 2.20–2.05 (m, 6H), 1.90–1.70 (m, 12H). $^{13}$C NMR (125 MHz, $CDCl_3$, 20° C.): 171.5, 166.1, 152.5, 141.9, 131.3, 130.8, 130.7, 129.4, 128.3, 128.0, 127.9, 127.3, 126.0, 125.3, 125.1, 125.1, 125.0, 124.8, 124.6, 123.2, 120.5–108.2 (several CF multipletts), 108.1, 72.6, 69.1, 69.0, 68.4, 64.1, 64.0, 39.3, 30.6 (t, $J_{CF}$=22 Hz), 29.7, 28.6, 17.3, 17.1. MALDI: 1923.11 (M+H$^+$); 1946.22 (M+Na$^+$+H$^+$); 1962.20 (M+K$^+$+H$^+$). DSC: 1st heating: k 49 (11.0) $\Phi_h$ 97 (0.5) i, 2nd heating: g –2 k 19 (2.3) $\Phi_h$ 97 (0.5) i, 1st cooling: i 92 (–0.4) $\Phi_h$ 7 g.

Example 4

Preparation of [4-(1-Pyrenyl)-butyl]3,4,5-tris-(12,12,12,11,11,10,10,9,9,8,8,7,7,6,6,5,5-heptadecafluoro-n-dodecan-1-yloxy)-benzoate (D4)

As depicted in the Scheme below, 1-pyrenebutanol is reacted with 3,4,5-tris-(12,12,12,11,11,10,10,9,9,8,8,7,7,6,6,5,5-heptadecafluoro-n-dodecan-1-yloxy)-benzoic acid to produce a fourth representative mobility donor fluorinated dendron of the present invention, D4.

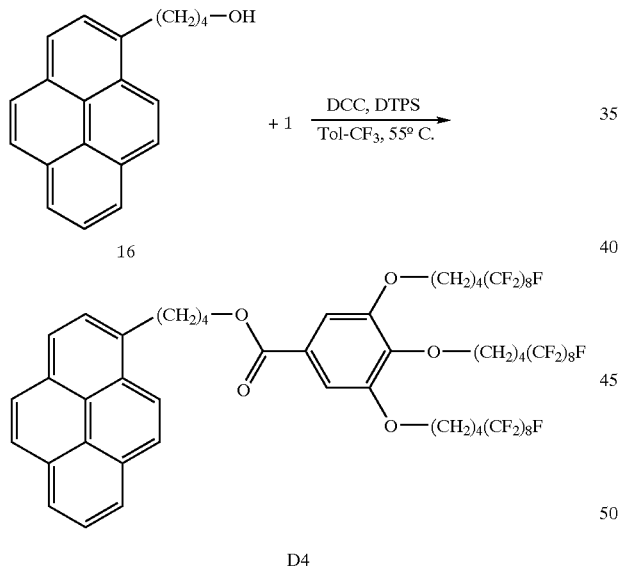

More particularly, compound D4 is synthesized as follows:

[4-(1-Pyrenyl)-butyl]3,4,5-tris-(12,12,12,11,11,10,10,9,9,8,8,7,7,6,6,5,5-heptadecafluoro-n-dodecan-1-yloxy)-benzoate (D4): To a solution of 1 (0.5 g, 0.31 mmol), 1-pyrenebutanol 16 (95 mg, 0.34 mmol) and DPTS (20 mg, 65.4 μmol) in α,α,α-trifluorotoluene (20 ml) under $N_2$ was added DCC (140 mg, 0.68 mmol), and the reaction mixture was stirred at 45° C. for 24 h. The reaction mixture was cooled to 20° C. and the product was precipitated in MeOH which was subsequently precipitated in MeOH three times from $CH_2Cl_2$ solution. The crude product was purified by column chromatography ($SiO_2$, $CH_2Cl_2$) and followed by precipitating in EtOH from $CH_2Cl_2$ solution yielded 320 mg (55%) of D4 as white solid. TLC: Rf=0.52 ($CH_2Cl_2$/hexanes: 2/1). Purity: 99%+: (HPLC). $^1$H NMR ($CDCl_3$, 200 MHz, 20° C.): d 8.26 (d, 1H, J=7.6 Hz), 8.18–7.98 (m, 7H), 7.89 (d, 1H, J=7.8 Hz), 7.24 (s, 2H), 4.4 (t, 2H, J=6.0 Hz), 3.98 (m, 6H), 3.44 (t, 2H, J=7.3 Hz), 2.13 (m, 8H), 1.81 (m, 14H). $^{13}$C NMR ($CDCl_3$, 90 MHz, 20° C.): d 166.2, 152.5, 141.8, 131.7, 131.1, 130.2, 128.8, 127.8, 127.7, 127.5, 127.1, 126.1, 125.8, 125.2, 125.0, 123.5, 120.5–108.2 (several CF multipletts), 107.9, 72.6, 68.2, 64.9, 33.0, 30.7 (t, $J_{CF}$=22 Hz), 30.4, 28.7, 28.6, 28.2, 17.3, 17.1. FAB-MS (m/z): 1871.2 [M+Na]+. Anal. Calcd. for $C_{63}H_{43}F_{31}O_3$ C, 41.19; H 2.58; found C, 41.04; H, 2.08. DSC: 1st heating k 59 (8.2) k 63 (–11.0) k 83(11.7), k 90 (11.2) i, 1st cooling i 78 (0.5) $\Phi_h$ 2 g. 2nd heating g –1.0 k 13 (1.3) $\Phi_h$ 82 (0.6) i.

Example 5

Preparation of 2-[2-(4,5,7-Trinitro-9-fluorenone-2-carboxy)-ethoxy]-ethyl 3,4,5-tris-(12,12,12,11,11,10,10,9,9,8,8,7,7,6,6,5,5-Heptadecafluoro-n-dodecan-1-yloxy)benzoate (A1)

As depicted in the Scheme below, [2-(2-Hydroxyethoxy)-ethyl](4,5,7-trinitro-9-fluorenone)-2-carboxylate is reacted with 3,4,5-tris-(12,12,12,11,11,10,10,9,9,8,8,7,7,6,6,5,5-heptadecafluoro-n-dodecan-1-yloxy)-benzoic acid to produce a representative mobility acceptor fluorinated dendron of the present invention, compound A1.

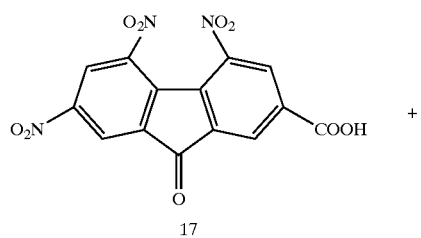

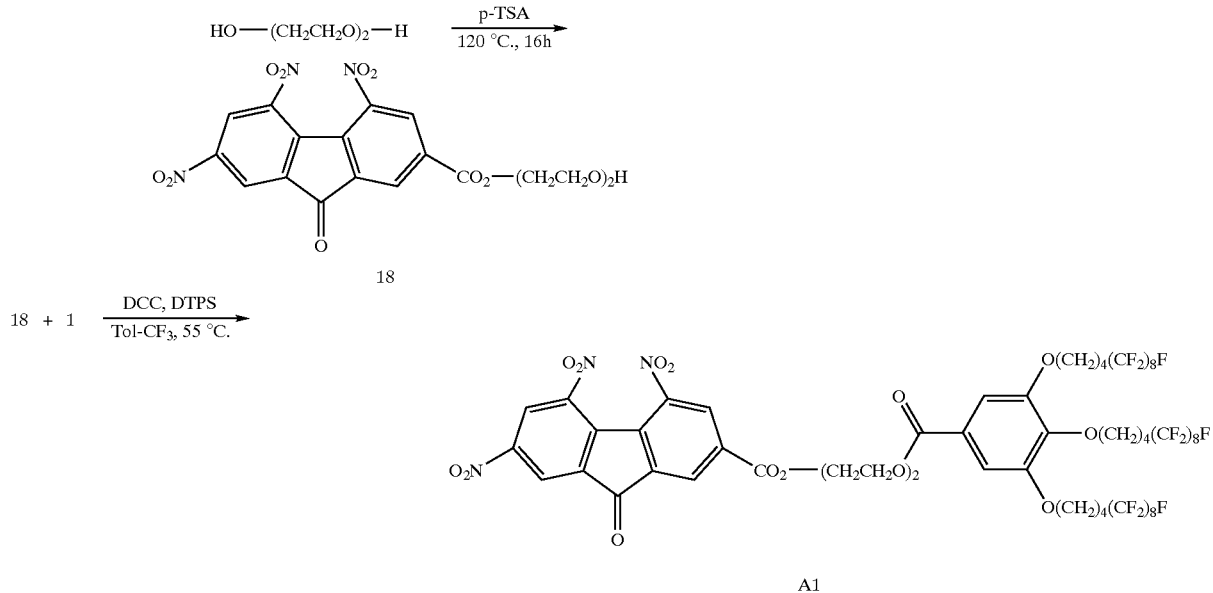

More particularly, compound A1 is synthesized as follows:

[2-(2-Hydroxyethoxy)-ethyl](4,5,7-trinitro-9-fluorenone)-2-carboxylate (18): A mixture of 4,5,7-trinitro-9-fluorenone-2-carboxylic acid 17 (2.0 g, 5.6 mmol), diethylene glycol (4 ml, 36.4 mmol) and 100 mg (0.58 mmol) of PTSA was stirred at 120° C. under $N_2$. The reaction mixture became homogeneous after 1 h and the stirring was continued overnight (12 h). The reaction mixture was cooled to 20° C. and poured into a mixture of ice and $H_2O$ (50 ml) drop-wise. The crude product was separated from $H_2O$ as a light brown solid. Column chromatography ($SiO_2$, hexanes/EtOAc: 60/40) followed by recrystallization from ethanol yielded 1.6 g (65%) of 18 as brown crystals. Purity: 99% (HPLC). TLC: Rf=0.1 (hexanes/EtOAc: 3/1). mp 140° C. $^1$H NMR (200 MHz, $CDCl_3$, 20° C.): d 8.99 (d, 1H, J=2 Hz), 8.89 (t, 2H, J=2 Hz), 8.75 (d, 1H, J=2 Hz), 4.60–4.64 (q, J=4Hz, 2H), 3.91–3.89 (q, 2H, J=4 Hz), 3.81–3.77 (q, 2H, J=4.1 Hz), 3.65–3.69 (q, 2H, J=4 Hz). $^{13}$C NMR (50 MHz, $CDCl_3$, 20° C.) d 186.43, 162.03, 149.96, 147.08, 146.81, 138.70, 138.63, 137.95, 135.75, 131.95, 129.56, 125.70, 122.19, 72.82, 69.09, 65.90, 62.04.

2-[2-(4,5,7-trinitro-9-fluorenone-2-carboxy)-ethoxy]-ethyl 3,4,5-tris-(12,12,12,11,11,10,10,9,9,8,8,7,7,6,6,5,5-Heptadecafluoro-n-dodecan-1-yloxy) benzoate (A1): A mixture containing 1 (1.0 g, 0.63 mmol) and 18 (0.295 g, 0.65 mmol) was dissolved in α,α,α-trifluorotoluene (10 ml) and stirred over molecular sieves (4 Å) for 1 h under $N_2$. DCC (0.260 g, 1.26 mmol) and DPTS (40 mg, 0.13 mmol) were added to the reaction mixture. The reaction mixture was stirred at 45° C. for 24 h under $N_2$. The progress of the reaction was monitored by TLC (hexanes/EtOAc: 75/25) (Rf=0.75). The reaction mixture was filtered through a sintered funnel and the molecular sieves were washed several times with $CH_2Cl_2$. The organic solution was concentrated and precipitated in MeOH four times from $CH_2Cl_2$ solution. The crude product was purified by column chromatography ($SiO_2/CH_2Cl_2$) to yield 1.08 g (85%) orange crystals. $^1$H NMR ($CDCl_3$, 500 MHz, 20° C.): d 9.09–9.10 (d, 1H, J=2 Hz), 8.93–8.85 (t, 2H, J=2 Hz), 8.71–8.70 (d, 1H, J=2 Hz), 7.39 (s, 2H), 4.76–4.71 (q, 2H, J=4 Hz), 4.62–4.58 (q, 2H, J=4 Hz), 4.12–4.09 (m, 6H) 4.03–4.01 (m, 4H), 2.33–2.20 (m, 6H), 1.99–1.85, 1.70–1.38 (m, 12H). $^{13}$C NMR ($CDCl_3$, 90 MHz, 20° C.): d 184.78, 165.91, 162.73, 152.51, 149.70, 146.73, 146.53, 140.42, 138.58, 137.65, 135.25, 131.48, 128.96, 125.25, 125.1, 122.52, 120.5–108.2 (several CF multipletts), 108.03, 105.73, 72.67, 69.18, 68.48, 65.36, 63.75, 31.17 (t, $J_{CF}$=22 Hz), 29.75, 28.83, 17.3–17.17. Anal. Calcd for $C_{61}H_{38}N_3F_{51}O_{15}$: C, 36.24; H, 1.89; F, 47.92; N, 2.08. Found: C, 36.41; H, 1.79; N, 1.92. DSC: 1st heating k 50 (2.0) $\Phi_{r-c}$ 121 (0.4) i, 1st cooling i 115 (0.4) $\Phi_{r-c}$ 33 g. 2nd heating g 34 $\Phi_{r-c}$ 121 (0.4) i.

Example 6

Preparation of Poly([2-(2-carbazol-9-yl-ethoxy)-ethyl]methacrylate) (DP2)

[2-(2-Carbazol-9-yl-ethoxy)-ethyl]methacrylate (20): 1.05 g (4.12 mmol) 4 and 0.65 g (6.22 mmol) methacryloyl chloride were dissolved in 15 ml of carbon tetrachloride. After the addition of 2.6 g activated molecular sieves (3 Å), the mixture was heated to reflux for 24 h. After cooling down to room temperature, it was filtered over basic alumina using 20% THF in $CCl_4$. Evaporating the solvent yielded 0.8 g (60.1%) of a viscous yellow oil. Rf=0.44 (EtOAc/hexanes: 2/8). $^1$H NMR ($CDCl_3$, 500 MHz, 20° C.): d 8.10 (t, 2H, J=7.76 Hz), 7.44 (m, 4H), 7.23 (m, 2H), 5.99 (s, 1H), 5.51 (s, 1H), 4.49 (t, 2H, 5.95 Hz), 4.19 (t, 2H, J=4.75 Hz), 3.88 (t, 2H, J=5.95 Hz), 3.59 (t, 2H, J=4.75 Hz), 1.88 (s, 3H). $^{13}$C NMR ($CDCl_3$, 125 MHz, 20° C.): d 167.3, 140.6, 136.0, 125.8, 125.7, 122.9, 120.3, 119.0, 108.8, 69.5, 69.3, 63.7, 43.2, 18.2.

Poly([2-(2-Carbazol-9-yl-ethoxy)-ethyl]methacrylate) (DP2): A Schlenk tube was charged with 2.1 ml 1,4-dioxane, 0.5 g (1.55 mmol; 23.8% w/v) 20 and 30.0 mg AIBN (6%). The reaction mixture was degassed six times and the polymerization was carried out at 60° C. for 48 h. The polymer was purified by precipitation of the crude polymer from THF solution three times into methanol. The molecular weights related to poly (styrene) standards were determined in THF. Mn=11,400. Mw/Mn=1.96. $^1$H NMR ($CDCl_3$, 500 MHz, 20° C.): d 7.91 (br, 2H), 7.29–7.04 (br, 6H), 4.15 (br, 2H), 3.82

(br, 2H), 3.48 (br, 2H), 3.20 (br, 2H), 1.94–1.87 (br, 2H), 1.20–0.90 (br, 3H).

Example 7

Preparation of Poly(2-{2-[2-(2-methacryloyloxyethoxy)-ethoxy]-ethoxy}-ethyl 4,5,7-Trinitrofluoren-9-one-2-carboxylate) (AP1)

2-{2-[2-(2-hydroxyethoxy)-ethoxy]-ethoxy}-ethyl 4,5,7-trinitro-fluoren-9-one-2-carboxylate (22): 1 g (2.78 mmol) 17, 15 ml (86.6 mmol) dry tetraethylene glycol and 100 mg (0.58 mmol) p-toluenesulfonic acid were dissolved in toluene (100 ml). The flask was equipped with a water receiver and the reaction mixture was heated to reflux for 16 h. After removing the toluene, ethyl acetate was added and extracted with water for two times. The ethyl acetate was evaporated and the product was filtered over a short silica gel column using 30% hexanes in ethyl acetate as eluent. The solvent was removed and the product was precipitated from $CH_2Cl_2$ into hexanes to yield 0.83 g (55.8%) of a highly viscous dark red oil. Rf=0.29 (EtOAc). $^1$H NMR ($CDCl_3$, 500 MHz, 20° C.): d 8.98 (s, 1H), 8.85 (s, 2H), 8.76 (s, 1H), 4.61 (t, 2H, J=4.6 Hz), 3.89 (t, 2H, J=4.7 Hz), 3.70 (m, 10H), 3.59 (t, 2H, J=4.7 Hz), 2.30 (s br, 1H). $^{13}$C NMR ($CDCl_3$, 125 MHz, 20° C.): d 184.9, 162.7, 149.6, 146.8, 146.5, 138.5, 138.4, 137.6, 136.1, 135.6, 131.8, 129.4, 125.4, 122.6, 72.5, 70.7, 70.6, 70.5, 70.3, 68.8, 65.7, 61.7.

2-{2-[2-(2-methacryloyloxyethoxy)-ethoxy]-ethoxy}-ethyl 4,5,7-trinitrofluoren-9-one-2-carboxylate (23): 0.7 g (1.3 mmol) 22, 0.15 g (1.44 mmol) 19 and 0.5 g activated molecular sieves (4 Å) were added to dry THF (10 ml). After the mixture was cooled to 0° C., 0.15 g (1.44 mmol) triethylamine was added. Then it was allowed to reach room temperature and was stirred for three hours. Ammonium salts were filtered off, the THF was evaporated and the crude product was redissolved in chloroform. The solution was extracted three times with diluted potassium hydroxide solution, two times with water, one time with brine and was then dried over magnesium sulfate. After the chloroform was evaporated, the monomer was purified by column chromatography on silica gel using 50% ethyl acetate in hexanes as eluent. The evaporation of the solvent yielded 0.4 g (51%) of a viscous dark orange oil. Rf=0.37 (EtOAc/hexanes: 1/1). $^1$H NMR ($CDCl_3$, 500 MHz, 20° C.): d 8.99 (s, 1H), 8.85 (m, 2H), 8.74 (s, 1H), 6.10 (s, 1H), 5.56 (s, 1H), 4.60 (m, 2H), 4.28 (m, 2H), 3.88 (m, 2H), 3.71 (m, 10H), 1.93 (s, 3H). $^{13}$C NMR ($CDCl_3$, 125 MHz, 20° C.): d 184.9, 162.6, 149.6, 146.8, 138.5, 138.4, 137.6, 136.2, 136.1, 135.5, 131.7, 129.3, 125.7, 125.3, 122.6, 70.7, 69.1, 68.8, 65.7, 63.8, 18.3.

Poly(2-{2-[2-(2-methacryloyloxyethoxy)-ethoxy]-ethoxy}-ethyl 4,5,7-trinitrofluoren-9-one-2-carboxylate) (AP1): A Schlenk tube was charged with 0.8 ml 1,4-dioxane, 0.3 g (1.55 mmol; 37.5% w/v) 23 and 55.0 mg AIBN (18.3%). The reaction mixture was degassed six times and the polymerization was carried out at 60° C. for 36 h. The polymer was purified by precipitation of the crude polymer from THF solution three times into methanol. The molecular weights related to poly(styrene) standards were determined in THF. Mn=11,000. Mw/Mn=2.07. $^1$H NMR ($CDCl_3$, 500 MHz, 20° C.): 8.94–8.56 (m br, 4H), 4.58 (s br, 2H), 4.27–3.70 (m br, 14H), 1.86 (s br, 3H), 1.4–0.7 (m, br, 2H).

Example 8

Preparation of Poly(-vinyl Carbazole) (DP1)

Poly(-vinyl carbazole) (DP1): The polymerization of vinyl carbazole was carried out in benzene (50%, w/v) under $N_2$ at 60° C. AIBN (5%) was used as a radical initiator. The polymerization was terminated by diluting the polymerization mixture with $CH_2Cl_2$ and by precipitating in MeOH. The polymer was fractionated using $CH_2Cl_2$ as solvent (1%, w/v) and MeOH as nonsolvent at 20° C. into following fractions. Fraction 1: Mn=6,450 (Mw/Mn: 1.47). Fraction 2: Mn=12,100 (Mw/Mn: 1.75). Fraction 3: Mn=28,600 (Mw/Mn: 1.38). Fraction 4: Mn=57,450 (Mw/Mn: 1.49). Fraction 5: Mn=67,350 (Mn/Mw: 1.28).

Example 9

Preparation of Nanocylinder Compositions

Carbazole derivatives (D1), naphthalene derivatives (D2) and pyrene derivatives (D3 and D4) have been introduced at the apex as D, and 4,5,7-trinitrofluorenone-2-carboxylic acid (TNF) as A (A1), as discussed above, to produce fluorinated dendrons of the present invention having desired D, A, or D-A characteristics. A diethylene glycol or tetraethylene glycol spacer between the dendron and the D or A groups decouples their motion and facilitates fast self-assembly dynamics. In addition to this extraordinary simplicity, and diversity in synthesis, the self-assembled D and A groups are protected from moisture by the internal compartmentalization of the cylinder and external jacketing with the fluorinated coat.

Co-assembling a D-dendron with an A-dendron incorporates an electron donor-acceptor (EDA) complex in the center of the cylinder (for example, A1+D1). Amorphous polymers with A and D side groups form EDA complexes when the D-dendron (for example, D1) is mixed with an A-polymer (for example, AP1) and when an A-dendron (for example, A1) is mixed with a D-polymer (for example, DP1 or DP2). Surprisingly, these EDA complexes self-assemble into cylinders that are self-organized into $\Phi_h$ or $\Phi_r$ LCs. We expect that the driving force of the fluorophobic effect is so strong that the complexed polymer is forced to reside in the center of the cylinder. EDA interactions, rather than the previously reported covalent bonding, are generating a supramolecular polymer with dendritic side groups. Nevertheless, as in the previous case, the random-coil conformation of the backbone becomes organized by jacketing with its dendritic side groups. The self-assembly and self-organization into $\Phi_h$ (D1, D2, D3, D4, D1+A1, A1+DP1, A1+DP2), $\Phi_{r-s}$ (D1+AP1) and $\Phi_{r-c}$ (A1) LCs was demonstrated by a combination of techniques, including differential scanning calorimetry (DSC), thermal optical polarized microscopy (TOPM), X-ray diffraction (XRD), and electron diffraction (ED). Calculations based on density and XRD measurements indicate that between 3.8 and 4.6 dendrons self-assemble into a 4.8 Å stratum of the cylinder. These self-processed systems consist of $4.5 \times 10^{12}$ to $5.8 \times 10^{12}$ cylinders per square centimeter. Accordingly, these systems are about two orders of magnitude denser than previously reported examples.

Table 1 summarizes the structures and the field and temperature independent $\mu_e$ and $\mu_h$ values of the supramolecular assemblies determined by the time of flight (TOF) method. D-dendrons lead to $\mu_h$ ranging from $10^{-4}$ to $10^{-3}$ cm$^2 \cdot$V$^{-1} \cdot$s$^{-1}$ in the LC state whereas the A-dendron (A1) has an $\mu_e$ of $10^{-3}$ cm$^2 \cdot$V$^{-1} \cdot$s$^{-1}$. The $\mu$ of the EDA polymer complexes are in the same range. All these values are from two to five orders of magnitude higher than those of the related D and A compounds in the amorphous state (see Table 1). We expect that this enhancement is due to the p-stacked one-dimensional ordered structure of D, A or EDA complex in the center of the supramolecular column. The charge migration through the columns is not well understood, but we believe that it involves a polaron hopping process. XRD and $^1$H-NMR studies demonstrate p-p-interactions between the D or A groups. The $\mu$ of these very simple D-dendrons is similar to those of more complex discotic LCs. Higher $\mu$ reported on these discotic molecules was obtained either in the $\Phi_{ho}$ crystal phase or was measured by contactless pulse-radiolysis time-resolved microwave conductivity (PR-TRMC) that provides the one-dimensional intracolumnar mobility. TOF data are inherently lower, accounting for the structural imperfections within the inter-electrode gap but are more relevant for technical applications than the higher values obtained by PR-TRMC.

Cooling the LC state leads to crystallization in the case of D2, whereas the 2-D order of D1, D3 and A1 is enhanced in the glassy state, showing helical short-range order. For example, the XRD of a fiber of A1 in the glassy ordered state cooled from the LC phase exhibits, in the small-angle region, the pattern of the $\Phi_h$ order (FIG. 1). This demonstrates that the LC order is frozen into a glassy $\Phi_h$ state. In addition, at wide-angle the XRD pattern reveals diffuse spots arranged in an x-like fashion that indicates short-range helical correlation along the column axis with an average repeat distance of 4.8±0.3 Å ("E" in FIG. 1). We expect that this value arises from the packing of the aromatic regions of the dendron near the aliphatic tails. This XRD also shows diffuse spots assigned to disordered p-stacks of TNF units in the core of the column with an average separation of 3.44 Å ("C" in FIG. 1). Consequently, $\mu$ of this glassy LC state increases since the motion of the D groups from the core of the supramolecular cylinder is decreased, leading to reduced dynamic disorder (Table 1). Furthermore, the motion of ionic impurities is frozen in the ordered state, whereas the photo-generated charges continue to migrate within the system. Therefore, the glassy ordered state is essentially insensitive to ionic impurities.

FIG. 2 depicts $^1$H NMR spectra of A1 in CDCl$_3$ solution at 22° C., in the isotropic melt at 120° C., in the $\Phi_h$ LC state at 75° C. and in the $\Phi_h$ glassy state at 25° C. In this sequence, the loss of molecular mobility is reflected by the increase of the line widths. As fast magic-angle spinning is applied (except for the solution), four groups of $^1$H resonances can be distinguished in all spectra: aromatic fluorenone (9–8 ppm), dendron phenyl (7–6 ppm), OCH$_2$ (4.5–3 ppm), and alkyl (2.5–1 ppm). In the glass, the LC phase and the melt, the lines are shifted to high field by 0.5–0.7 ppm relative to the solution-state values except for the alkyl resonances. This effect is due to aromatic p-electrons situated above or below the respective protons, and thus provides direct evidence for p-p packing of the fluorenones and the dendron phenyls. Analogous effects are observed in the $^1$H spectra of the other materials. Moreover, in A1 a distance of 3.5 Å was determined between the protons in adjacent fluorenone moieties by $^1$H—$^1$H double-quantum NMR spectroscopy, which leads to the expectation of a sandwich-type packing of pairs of nitro-fluorenone groups (FIG. 2e). Combining the NMR information with the XRD data, it can be concluded that, in the glassy $\Phi_h$ phase, the cylinder adopts a supramolecular structure of the form schematically depicted in FIG. 2f. In the center, the fluorenone sandwiches are stacked in a column surrounded by dendrons whose phenyl groups are arranged in a helical fashion around the central column. Furthermore, NMR data provides evidence for the separation of the fluorenones (center), dendron phenyls (inner ring) and alkyl chains (outer ring) from each other, as there are no proton-proton distances detectable between the different units on a length scale of less than 4 Å. This separation, however, is not completely achieved when the material is precipitated from solution, but only when the system is enabled to self-organize in the course of a cooling process from the melt into the LC and glassy $\Phi_h$ phases. Prior to this process the supramolecular column contains errors introduced by intramolecular backfolded A1 dendrons. A self-repair process occurs during cooling from the isotropic melt. The supramolecular structure from FIG. 2f in some ways resembles that of base-pairs in DNA.

Tables 2–5 summarize the structural analysis of A and D dendrons and of their EDA complexes, as well as the EDA complexes of A and D dendrons with amorphous polymers containing D and A side groups by XRD experiments. The charge carrier mobilities of amorphous polymers and the acceptor compound available in the literature are reported in Tables 4 and 5. Charge carrier mobilities determined by TOF are reported in Tables 2 and 5.

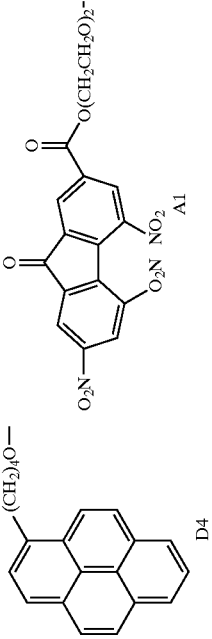

TABLE 2

Thermal transitions, X-ray results, and charge carrier mobilities ($\mu_h$ and $\mu_e$) of compounds D1–D4 and A1.

| Compound | Transition temperatures (° C.) and enthalpy changes (kcal·mol$^{-1}$) | d-spacings and lattice dimensions (Å) at T (° C.) | $\mu_h$ and $\mu_s$ (cm$^2$·V$^{-1}$·s$^{-1}$) Phase and T (° C.) |
|---|---|---|---|
| D1 | k 39 (2.3) k 53 (9.6) $\Phi_h$ 75 (1.0) i<br>g 13 k 21 (5.0) $\Phi_h$ 75 (0.8) i<br>i 71 (−0.8) $\Phi_h$ 13 (−4.9) k 6 g | $\Phi_h$:d$_{10}$ (39.0) d$_{11}$ (22.4) d$_{20}$ (19.5)<br><a> (44.9)<br>T (61) | 1.3 · 10$^{-3}$ ($\Phi_h$, 65, h)<br>5.0 · 10$^{-3}$ (g, 18, h) |
| D2 | k 24 (0.7) k 48 (8.9) $\Phi_h$ 74 (0.4) i<br>g 11 k 24 (3.0) $\Phi_h$ 74 (0.4) i<br>i 70 (−0.4) $\Phi_h$ 16 (−3.2) k | $\Phi_h$:d$_{10}$ (40.8) d$_{20}$ (20.1) <a> (46.8)<br>T (36) | 3.5 · 10$^{-3}$ ($\Phi_h$, 50, h) |
| D3 | k 49 (11.0) $\Phi_h$ 97 (0.5) i<br>g −2 k 19 (2.3) $\Phi_h$ 97 (0.5) i<br>i 92 (−0.4) $\Phi_h$ 7 g | $\Phi_h$:d$_{10}$ (42.5) d$_{11}$ (24.2) d$_{20}$ (20.9)<br><a> (48.6) T (30) | 9.4 · 10$^{-4}$ ($\Phi_h$, 60, h)<br>1.3 · 10$^{-3}$ (g, 18, h) |
| D4 | k 59 (8.2) k 63 (−11.0) k 83 (11.7)<br>k 90 (11.2) i<br>g −1 k 13 (1.3) $\Phi_h$ 82 (0.6) i<br>i 78 (−0.5) $\Phi_h$ 2 g | $\Phi_h$:d$_{10}$ (39.0) d$_{11}$ (22.3) d$_{20}$ (19.2)<br><a> (44.6) T (60) | 1.5 · 10$^{-3}$ ($\Phi_h$, 55, h) |
| A1 | k 50 (2.0) $\Phi_{r-c}$ 121 (0.4) i<br>g 34 $\Phi_{rc}$ 121 (0.4) i<br>i 115 (−0.4) $\Phi_{r-c}$ 33 g | $\Phi_{r-c}$*:d$_{11}$ (44.3) d$_{02}$ (41.3) d$_{20}$ (25.5)<br>d$_{22}$ (21.8) d$_{04}$ (20.5) a (51.4)<br>b (82.0)<br>b/a = 1.60 T (25) | 2.0 · 10$^{-3}$ ($\Phi_{r-c}$, 50, e)<br>7.5 · 10$^{-3}$ (g, 10, e) |

*In the centered rectangular lattice ($\Phi_{r-c}$), the columns with elliptical cross-section are centered at the corners as well as the center of the rectangular unit cell.

TABLE 3

Densities ρ of compounds D1–D4 and A1, number of molecules per cylinder stratum of 4.8 Å ($N_m$), and number of columns per cm$^2$ ($N_c$).

| Compound | Density ρ (g · cm$^{-3}$) | $N_m$* | $N_c$ (cm$^{-2}$) |
|---|---|---|---|
| D1 | 1.62 | 4.54 | 5.73 · 10$^{12}$ |
| D2 | 1.49 | 4.42 | 5.27 · 10$^{12}$ |
| D3 | 1.49 | 4.58 | 4.89 · 10$^{12}$ |
| D4 | 1.53 | 4.12 | 5.81 · 10$^{12}$ |
| A1 | 1.25 | 3.76 | 4.75 · 10$^{12}$ |

*For the $\Phi_h$ lattice: $N_m = \dfrac{\rho \cdot \sqrt{3} \cdot a^2 \cdot l \cdot N_A}{2M_w}$;

for the $\Phi_{r-c}$ lattice: $N_m = \dfrac{\rho \cdot a \cdot b \cdot l \cdot N_A}{2M_w}$ with:

a, b = lattice dimensions, I = 4.8 Å (thickness of the stratum), $N_A$ = Avogadro's number, $M_w$ = molecular weight.

†For the $\Phi_h$ lattice: $N_c = \dfrac{2}{\sqrt{3} \cdot a^2}$;

for the $\Phi_{r-c}$ lattice: $N_c = \dfrac{2}{a \cdot b}$.

TABLE 4

Molecular weights ($M_n$), polydispersities ($M_w/M_n$) and glass transition temperatures ($T_g$) of DP1, DP2 and AP1 and charge carrier mobilities ($\mu$) of related polymers DP1 and AP2 reported in the literature.

| Polymer | $M_n$ ($M_w/M_n$) | $T_g$ (° C.) | $\mu_h$ and $\mu_s$ (cm$^2$ · V$^{-1}$ · s$^{-1}$) at T (° C.) |
|---|---|---|---|
| DP1 | 6,443 (1.47) | 77 | 1.5 · 10$^{-7}$ (25, h)* |
| DP2 | 11,426 (1.96) | 74 | 13 |
| DP3 | 31,000 (4.5)* | 146* | 9 · 10$^{-6}$ (25, h) |
| AP1 | 4: 11,041 (2.07) | 55 | — |
| AP2 | 1: 7,939 (1.88) | — | 2.8 · 10$^{-8}$ (25, e) † |

*Uryu, T., Ohkawa, H., Oshima, R. Macromolecules 20, 712–716 (1987).
†Turner, S. R. Macromolecules 13, 782–785 (1980).

TABLE 5

Thermal transitions, X-ray results and charge carrier mobility $\mu$ of prepared and related EDA complexes.

| EDA complexes | Transition temperatures (° C.) and enthalpy changes (kcal · mru$^{-1}$) | d-spacings and lattice dimensions (Å) at T (° C.) | $\mu_h$ and $\mu_s$ (cm$^2$ · V$^{-1}$ · s$^{-1}$) Phase and T (° C.) |
|---|---|---|---|
| DP1/A2 (50/50) | — | — | 2.0 · 10$^{-8}$ (24, h)*<br>2.0 · 10$^{-6}$ (24, e)* |
| D1/A1 (95/5) | k 23 (1.7) $\Phi_h$ 81 (0.6) i<br>g 16 k 23 (1.4) $\Phi_h$ 81 (0.5)<br>i 75 (−0.5) $\Phi_h$ 16 (−1.5) k 7 g | $\Phi_h$:d$_{10}$ (41.3)<br>d$_{20}$ (21.0)<br>d$_{30}$ (14.1)<br><a> (48.1) T (55) | 1.6 · 10$^{-3}$ ($\Phi_h$, 70, h) |
| A1/DP1 (50/50) | k 53 (1.2) $\Phi_h$ 124 (0.39) i | $\Phi_h$:d$_{10}$ (59.3) | 10$^{-4}$ ($\Phi_h$ 50, h) |

TABLE 5-continued

Thermal transitions, X-ray results and charge carrier mobility $\mu$ of prepared and related EDA complexes.

| EDA complexes | Transition temperatures (° C.) and enthalpy changes (kcal · mru$^{-1}$) | d-spacings and lattice dimensions (Å) at T (° C.) | $\mu_h$ and $\mu_s$ (cm$^2$ · V$^{-1}$ · s$^{-1}$) Phase and T (° C.) |
|---|---|---|---|
| A1/DP2 (50/50) | g 42 $\Phi_h$ 120 (0.23) i<br>i 107 (−0.24) $\Phi_h$ 35 g<br>k 54 (1.8) $\Phi_h$ 167 (0.1) i<br>g 46 $\Phi_h$ 168 (0.1) i<br>i 157 (−0.3) $\Phi_h$ 35 g | $d_{20}$ (29.6)<br><a> (68.5) T (87)<br>$\Phi_h$:$d_{10}$ (59.3)<br>$d_{20}$ (29.6)<br><a> (68.5) T (87) | <br><br>2.3 · 10$^{-4}$ ($\Phi_h$, 70, h)<br><br>1.5 · 10$^{-4}$ ($\Phi_h$, 70, e) |
| D1/AP1 (50/50) | g 33 k 43 (1.2) $\Phi_{r-c}$ 97 (0.1) N$_c$ 132 (0.4) i<br>g 26 $\Phi_{r-c}$ 99 (0.1) N$_c$ 132 (0.8) i<br>i 124 (−0.2) N$_c$ 87 (−0.1) $\Phi_{r-c}$ 29 g | $\Phi_{r-g}$ †:$d_{10}$ (62.8)<br>$d_{11}$ (53.7)<br>$d_{03}$ (37.4)<br>$d_{13}$ (31.9) a (61.8) b (111.9) T (71)<br>N$_c$:(63.8, 34.9)<br>b/a = 1.81 T (110) | 5.3 · 10$^{-4}$ ($\Phi_{r-g}$, 60, h)<br><br>4.8 · 10$^{-4}$ ($\Phi_{r-g}$, 60, e) |

Gill, W.D. J. Appl. Phys. 43, 5033–5040 (1972). †The columns with elliptical cross-section organize in a simple rectangular lattice ($\Phi_{r-s}$) with the columns centered at the corners of the rectangular unit cell.

Example 10

Charge Carrier Mobility of Nanocylinder Compositions

Purification of A and D dendrons and A and D polymers. A and D dendrons and A and D polymers were purified by precipitation from their CH$_2$Cl$_2$ solutions into methanol, followed by filtration and vacuum drying as many times as required to provide samples essentially free of ionic impurities. This level of purity was generally reached after about four precipitations. The absence of ionic impurities was determined by spectroscopy using the time of flight (TOF) method.

Sample Preparation. Liquid crystal cells were assembled from indium tin oxide (ITO) coated glass substrates. The cells were assembled by cementing two substrates separated by mylar spacers. These cells were then filled in the isotropic phase using the capillary effect, and then slowly cooled down to the liquid crystalline phase at a cooling rate of approximately 0.1° C./min. As a result, homeotropic alignment of LC films having the columnar long axis normal to the electrode surfaces was achieved. Polarizing optical microscopy revealed a large domain size, in the range of 200–300 $\mu$m. The cell thickness was controlled by the spacers and ranged from 11 to 50 $\mu$m. Because the thickness of LC layer was considerably smaller than the domain size, charge carriers can be transported from one electrode to the other without encountering domain boundaries. Because of the low charge generation efficiency in some of the films, double layer films that include a charge generation layer (CGL) were prepared. Metal-free phthalocyanine (H2Pc) was dispersed in polyvinyl butyral (PVB) (poly(vinyl butyral-co-vinyl alcohol-co-vinyl acetate, M.W. 50,000–80,000) in a ratio of 40:60% by weight. The CGL was deposited from tetrahydrofuran (anhydrous 99.9%) solution by spin coating onto ITO substrate. Deposited films were dried at 100° C. for 4 hours in order to remove the residual solvent. The CGL thicknesses were measured with a stylus profilometer and were found to be between 0.5 to 0.8 $\mu$m. Because of the rough surface of the CGL, alignment for double layer cells was performed by slow cooling from the isotropic phase in the presence of a 1 T magnetic field.

Charge Carrier Mobility—Time of Flight. A conventional time of flight technique was employed to measure the transient photocurrent and to determine the mobility of charge carriers. A 3.6 ns Q-switched Nd:YAG based laser that was frequency doubled and frequency shifted using a H$_2$ stimulated Raman shifter was used to generate the charge carriers in a constant electric field. Two different charge generation mechanisms (intrinsic and extrinsic) were used. The intrinsic excitation (without the CGL layer) of LC by laser irradiation ($\lambda$=320 nm, third anti-Stokes component of a 532 nm pump) into the main absorption band of LC resulted in the creation of electron-hole pairs in a very thin layer, light penetration depth less than 1 $\mu$m, near the illuminated electrode. Depending on the polarity of the applied electric field, one charge carrier was eliminated at the illuminated electrode, while the other one moves through the sample towards the counter electrode. The extrinsic excitation (with the CGL layer) was employed with laser irradiation at 680 nm (first Stokes component) into the main absorption band of the dye layer. Charge carriers were formed at the LC/H2Pc interface and injected in to the LC layer. The charge motion creates a displacement current, which was measured with a current to voltage converter and pre-amplifier, and then was digitized with an oscilloscope. The mobility was calculated using the well-known relation $\mu = l^2/\tau_T V$, where l is the thickness of the charge transport layer, $\tau_T$ is the transit time, and V is the applied voltage. Both dispersive and non-dispersive transients were observed depending on the material and degree of alignment. For dispersive transients, we verified that the transients were not due to trap-limited transport by insuring that the transit time scaled linearly with the sample thickness (for several thicknesses). For dispersive transients, the transit time, $\tau_T$ was defined as the intercept of the asymptotes to pre- and post-transit slopes of the photocurrent plotted in the double logarithmic scale. For non-dispersive transients the transit time was given by the location of a well-defined knee. Typical time of flight transients are shown in FIG. 2. As indicated in FIG. 3, the mobility was found to be relatively independent of electric field and temperature. The pulse energy was controlled by neutral density filters and kept below 10 $\mu$J/pulse to prevent the space charge build-up. Samples were mounted onto a heating stage with a temperature controller.

Example 11

Electron Diffraction (ED) of Nanocylinder Compositions

Due to the high sensitivity of the D4 ordered structure on electron beam, low-dose EM techniques were employed, including use of a small condenser aperture, small spot size, and reduced beam current and intensity to preserve the specimen integrity. Electron diffraction pattern of ordered domains was recorded at ED mode at a camera length of 120 cm. The images of ED pattern were accurately enlarged and printed, then scanned into the computer and analyzed.

FIG. 4 indicates a homeotropic alignment of hexagonal columnar phase of Pyr-F. The d-spacing of such material was calculated to be $<a>=42.9$ Å according to the Bragg's equation. In comparison, XRD showed a d-spacing of $<a>=44.6$ Å. Quantitative analysis of the diffraction spot intensity was carried out. In total, two unique reflections were found. Both reflections were strong. The ratio of intensity of these two reflections was 1:0.32. However, in order to compare with the XRD data, these intensities had to be multiplied by the respective multiplicity factor, which is 1:2. Thus, the ratio relative intensities are approximately 1:0.64. In comparison, XRD showed a ratio of 1:0.57.

The invention being thus described, it will be obvious that the same may be modified or varied in many ways. Such modifications and variations are not to be regarded as a departure from the spirit and scope of the invention and all such modifications and variations are intended to be included within the scope of the following claims.

I claim:

1. A compound of formula I

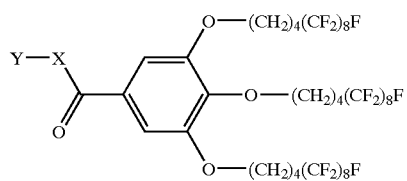

wherein:

X is $Z-(CH_2CH_2O)_n$, where n is 1–6, or $Z-(CH_2)_mO$, where m is 1–9;

Y is selected from the group consisting of pentalene, indene, naphthalene, azulene, heptalene, biphenylene, indacene, acenaphthylene, fluorene, phenalene, phenanthrene, anthrcene, fluoranthene, acephenanthrylene, aceanthrylene, triphenylene, pyrene, chrysene, and naphthacene, wherein said Y is optionally substituted with 1–6 substituents selected from the group consisting of nitro, nitroso, carbonyl, carboxy, oxo, hydroxy, fluoro, perfluoro, chloro, perchloro, bromo, perbromo, phospho, phosphono, phosphinyl, sulfo, sulfonyl, sulfinyl, trifluoromethyl, trifluoromethylsulfonyl, and trimethylsulfonyl, and wherein 1–4 carbon atom(s) of said Y is/are optionally replaced by N, NH, O, or S; and Z is selected from the group consisting of a direct bond, $-C(O)O-$, $(C_1-C_6 \text{ alkyl})-C(O)O-$, $(C_2-C_6 \text{ alkenyl})-C(O)O-$, and $(C_2-C_6 \text{ alkynyl})-C(O)O-$.

2. The compound of claim 1, wherein:

X is $Z-(CH_2CH_2O)_n$, where n is 1–3, or $Z-(CH_2)_mO$, where m is 2–4;

Y is selected from the group consisting of naphthalene, indacene, fluorene, phenahthrene, anthrcene, and pyrene, wherein said Y is optionally substituted with 1–4 substituents selected from the group consisting of nitro, carboxy, oxo, phospho, and sulfo, and wherein one carbon atom of said Y is optionally replaced by N or NH; and Z is selected from the group consisting of a direct bond, $-C(O)O-$, or $(C_1-C_6 \text{ alkyl})-C(O)O-$.

3. The compound of claim 1, wherein:

X is selected from the group consisting of diethylene glycol and tetraethylene glycol;

Y is selected from the group consisting of carbazole, naphthalene, pyrene, and 4,5,7-trinitrofluorenone-2-carboxylic acid; and Z is selected from the group consisting of a direct bond, $-C(O)O-$, and $-CH_2-C(O)O-$.

4. The compound of claim 1, wherein said compound is selected from the group consisting of:

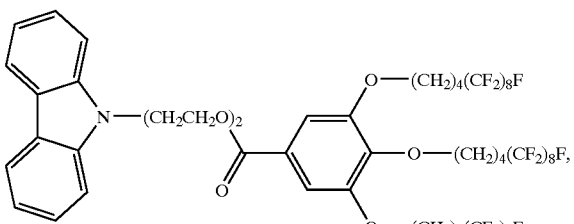

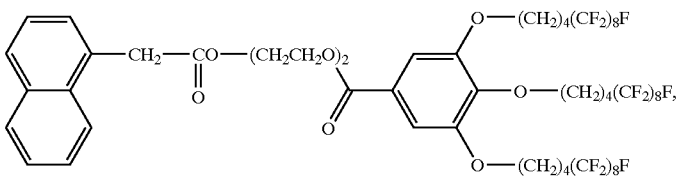

-continued

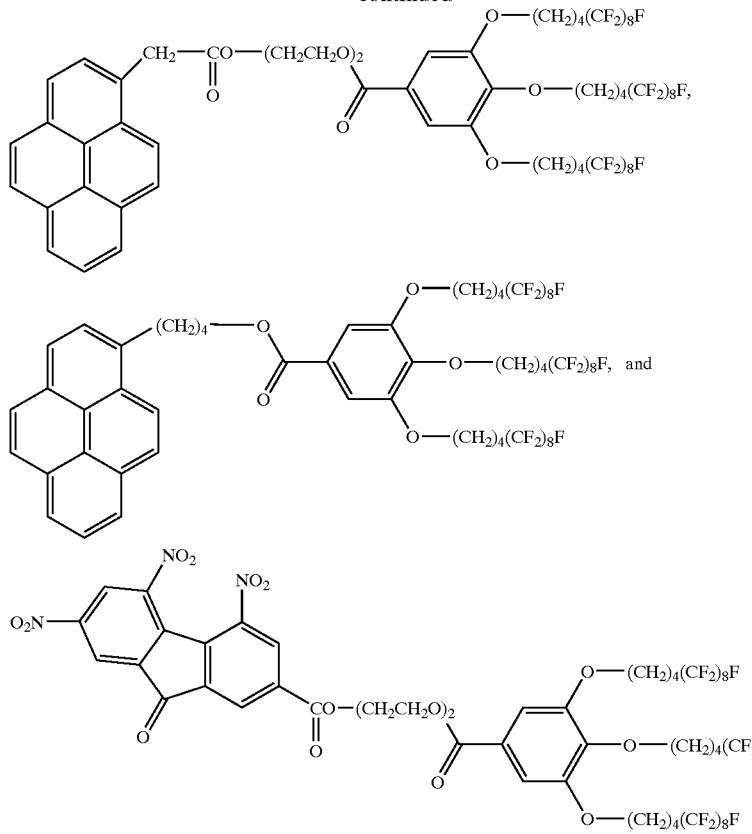

5. A process for making a stacked nanocylinder composition having a mobility donor complex, a mobility acceptor complex, or a mobility donor-acceptor complex in its core, which comprises:
   (a) heating semi-fluorinated dendrons incorporating selected dendron apex moiety(ies) and side group(s) having donor, acceptor, or donor-acceptor characteristics to an isotropic phase temperature;
   (b) filling a substrate with said isotropic phase dendrons; and
   (c) cooling said dendrons to a liquid crystalline phase temperature.

6. The process of claim 5, wherein said cooling step is in the presence of a magnetic field of about 1 tesla.

7. The process of claim 5, wherein said substrate is an indium tin oxide coated glass substrate.

8. The process of claim 5, wherein said cooling is at a rate of about 0.1° C. per minute.

9. The process of claim 5, wherein the substrate cell size of said nanocylinder composition is controlled by mylar spacers.

10. A stacked nanocylinder composition made by the process comprising the steps of:
   (a) heating semi-fluorinated dendrons incorporating selected dendron apex moiety(ies) and side group(s) having donor, acceptor, or donor-acceptor characteristics to an isotropic phase temperature;
   (b) filling an indium tin oxide coated glass substrate with said isotropic phase dendrons; and
   (c) cooling said dendrons to a liquid crystalline phase temperature at a rate of about 0.1° C. per minute, in the presence of a magnetic field of about 1 tesla.

* * * * *